United States Patent
Myung et al.

(10) Patent No.: US 12,227,592 B2
(45) Date of Patent: Feb. 18, 2025

(54) MONOCLONAL ANTIBODY SPECIFICALLY BINDING TO CCSP-2 AND USE THEREOF

(71) Applicants: THE ASAN FOUNDATION, Seoul (KR); EDISBIOTECH CO., LTD., Seoul (KR); UNIVERSITY OF ULSAN FOUNDATION FOR INDUSTRY COOPERATION, Ulsan (KR)

(72) Inventors: Seung-Jae Myung, Seoul (KR); Eun-Ju Do, Seoul (KR); Jayoung Kang, Buan-gun (KR); Hye-Nam Son, Seoul (KR); Hyori Kim, Seoul (KR); A-Neum Lee, Seoul (KR); Yeong Hui Cho, Hanam-si (KR)

(73) Assignees: THE ASAN FOUNDATION, Seoul (KR); EDISBIOTECH CO., LTD., Seoul (KR); UNIVERSITY OF ULSAN FOUNDATION FOR INDUSTRY COOPERATION, Ulsan (KR)

(*) Notice: Subject to any disclaimer, the term of this patent is extended or adjusted under 35 U.S.C. 154(b) by 620 days.

(21) Appl. No.: 17/310,296

(22) PCT Filed: Jan. 29, 2020

(86) PCT No.: PCT/KR2020/001370
§ 371 (c)(1),
(2) Date: Jul. 27, 2021

(87) PCT Pub. No.: WO2020/159229
PCT Pub. Date: Aug. 6, 2020

(65) Prior Publication Data
US 2022/0089774 A1    Mar. 24, 2022

(30) Foreign Application Priority Data
Jan. 29, 2019  (KR) ........................ 10-2019-0011172

(51) Int. Cl.
*C07K 16/00* (2006.01)
*C07K 16/32* (2006.01)
*G01N 33/574* (2006.01)

(52) U.S. Cl.
CPC ....... *C07K 16/32* (2013.01); *G01N 33/57492* (2013.01); *C07K 2317/56* (2013.01); *C07K 2317/565* (2013.01)

(58) Field of Classification Search
CPC ................ C07K 16/32; C07K 2317/56; C07K 2317/565; C07K 2317/622; C07K 2319/00; G01N 33/57492
See application file for complete search history.

(56) References Cited

U.S. PATENT DOCUMENTS

2011/0027283 A1    2/2011    Markowitz et al.
2019/0204321 A1    7/2019    Lee et al.

FOREIGN PATENT DOCUMENTS

| CN | 100342034 C | 10/2007 |
| KR | 10-2015-0105505 A | 9/2015 |
| KR | 10-2018-0009981 A | 1/2018 |
| KR | 10-2018-0060184 A | 6/2018 |
| WO | WO 2009/032292 A1 | 3/2009 |
| WO | WO 2018/016896 A1 | 1/2018 |

OTHER PUBLICATIONS

Mak and Saunders, Chapter-II, The Nature of Antigen-Antibody Interaction, Book the Immune Response, 2006 (Year: 2006).*
Sela-Culang et al (Frontiers in Immunology vol. 4, article 302, p. 1-13, 2013 (Year: 2013).*
Wilkinson et al (JBC 277: 5734-5741, 2002) (Year: 2002).*
Extended European Search Report issued Aug. 29, 2022, in corresponding European Patent Application No. 20747642.5, 12 pages.
International Search Report issued May 8, 2020 in PCT/KR2020/001370 filed Jan. 29, 2020, 2 pages.
Xin, B. et al., "Colon cancer secreted protein-2 (CCSP-2), a novel candidate serological marker of colon neoplasia", Oncogene, 2005, vol. 24, pp. 724-731, 9 total pages.
Kim, J. et al., "Molecular imaging of Colorectal Tumors by Targeting Colon Cancer Secreted Protein-2 (CCSP-2)", Neoplasia, vol. 19. No. 10, 2017, pp. 805-816.

* cited by examiner

*Primary Examiner* — Lei Yao
(74) *Attorney, Agent, or Firm* — Oblon, McClelland, Maier & Neustadt, L.L.P.

(57) ABSTRACT

The present invention relates to a monoclonal antibody which specifically binds to an EGF2 domain of colon cancer secreted protein-2 (CCSP-2), or an antigen-binding fragment thereof. The monoclonal antibody or the antigen-binding fragment thereof of the present invention specifically binds to the EGF2 domain of CCSP-2, and thus has significantly increased affinity compared with existing peptides specifically binding to CCSP-2 and further increased specificity compared with existing antibodies to CCSP-2. Therefore, in future, accurate diagnosis can be achieved by specific detection of CCSP-2 in the protein level.

8 Claims, 16 Drawing Sheets

Specification includes a Sequence Listing.

◆ Schematic diagram of CCSP-2 binding scFv antibody screening using EGF2 domain

1) Production of human-derived anti-EGF2 antibody

2) Chicken-derived anti-EGF2 antibody production

SEQUENCE LISTING

```
<160> NUMBER OF SEQ ID NOS: 70

<210> SEQ ID NO 1
<211> LENGTH: 7
<212> TYPE: PRT
<213> ORGANISM: Artificial Sequence
<220> FEATURE:
<223> OTHER INFORMATION: VH_CDR1 FOR HN-1

<400> SEQUENCE: 1

Gly Phe Thr Phe Ser Asp Arg
1               5

<210> SEQ ID NO 2
<211> LENGTH: 6
<212> TYPE: PRT
<213> ORGANISM: Artificial Sequence
<220> FEATURE:
<223> OTHER INFORMATION: VH_CDR2 FOR HN-1

<400> SEQUENCE: 2

Ser Asn Ala Gly Gly Tyr
1               5

<210> SEQ ID NO 3
<211> LENGTH: 9
<212> TYPE: PRT
<213> ORGANISM: Artificial Sequence
<220> FEATURE:
```

```
<223> OTHER INFORMATION: VH_CDR3 FOR HN-1

<400> SEQUENCE: 3

Gly Ala Ser Tyr Asp Ala Ile Asp Ala
1               5

<210> SEQ ID NO 4
<211> LENGTH: 7
<212> TYPE: PRT
<213> ORGANISM: Artificial Sequence
<220> FEATURE:
<223> OTHER INFORMATION: VL_CDR1 FOR HN-1

<400> SEQUENCE: 4

Ser Gly Ser Ser Arg Trp Tyr
1               5

<210> SEQ ID NO 5
<211> LENGTH: 7
<212> TYPE: PRT
<213> ORGANISM: Artificial Sequence
<220> FEATURE:
<223> OTHER INFORMATION: VL_CDR2 FOR HN-1

<400> SEQUENCE: 5

Ser Asn Asp Lys Arg Pro Ser
1               5

<210> SEQ ID NO 6
<211> LENGTH: 11
<212> TYPE: PRT
<213> ORGANISM: Artificial Sequence
<220> FEATURE:
<223> OTHER INFORMATION: VL_CDR3 FOR HN-1

<400> SEQUENCE: 6

Gly Ser Gly Asp Ser Ser Ser Asn Pro Gly Ile
1               5                   10

<210> SEQ ID NO 7
<211> LENGTH: 7
<212> TYPE: PRT
<213> ORGANISM: Artificial Sequence
<220> FEATURE:
<223> OTHER INFORMATION: VH_CDR1 FOR CH-1

<400> SEQUENCE: 7

Gly Phe Ser Phe Ser Gly Val
1               5

<210> SEQ ID NO 8
<211> LENGTH: 6
<212> TYPE: PRT
<213> ORGANISM: Artificial Sequence
<220> FEATURE:
<223> OTHER INFORMATION: VH_CDR2 FOR CH-1

<400> SEQUENCE: 8

Ser Ser Thr Gly Ser Gly
1               5

<210> SEQ ID NO 9
<211> LENGTH: 19
<212> TYPE: PRT
<213> ORGANISM: Artificial Sequence
<220> FEATURE:
<223> OTHER INFORMATION: VH_CDR3 FOR CH-1
```

-continued

<400> SEQUENCE: 9

Asp Ala Tyr Gly Tyr Arg Ile Ser Gly Ser Trp Ser Tyr Gly Tyr Ser
1               5                   10                  15

Ile Asp Ala

<210> SEQ ID NO 10
<211> LENGTH: 9
<212> TYPE: PRT
<213> ORGANISM: Artificial Sequence
<220> FEATURE:
<223> OTHER INFORMATION: VL_CDR1 FOR CH-1

<400> SEQUENCE: 10

Ser Gly Gly Ser Asn Ser Tyr Tyr Gly
1               5

<210> SEQ ID NO 11
<211> LENGTH: 7
<212> TYPE: PRT
<213> ORGANISM: Artificial Sequence
<220> FEATURE:
<223> OTHER INFORMATION: VL_CDR2 FOR CH-1

<400> SEQUENCE: 11

Asp Asn Thr Asn Arg Pro Ser
1               5

<210> SEQ ID NO 12
<211> LENGTH: 10
<212> TYPE: PRT
<213> ORGANISM: Artificial Sequence
<220> FEATURE:
<223> OTHER INFORMATION: VL_CDR3 FOR CH-1

<400> SEQUENCE: 12

Gly Ser Thr Asp Ser Ser Tyr Val Asp Ile
1               5                   10

<210> SEQ ID NO 13
<211> LENGTH: 7
<212> TYPE: PRT
<213> ORGANISM: Artificial Sequence
<220> FEATURE:
<223> OTHER INFORMATION: VH_CDR1 FOR CH-2

<400> SEQUENCE: 13

Gly Phe Thr Phe Ser Ser Val
1               5

<210> SEQ ID NO 14
<211> LENGTH: 6
<212> TYPE: PRT
<213> ORGANISM: Artificial Sequence
<220> FEATURE:
<223> OTHER INFORMATION: VH_CDR2 FOR CH-2

<400> SEQUENCE: 14

Ser Asn Thr Gly Ser Gly
1               5

<210> SEQ ID NO 15
<211> LENGTH: 19
<212> TYPE: PRT
<213> ORGANISM: Artificial Sequence
<220> FEATURE:

```
<223> OTHER INFORMATION: VH_CDR3 FOR CH-2

<400> SEQUENCE: 15

Asp Ala Tyr Gly Tyr Thr Ile Ser Gly Ser Trp Ser Tyr Gly Tyr Ser
1               5                   10                  15
Ile Asp Ala

<210> SEQ ID NO 16
<211> LENGTH: 8
<212> TYPE: PRT
<213> ORGANISM: Artificial Sequence
<220> FEATURE:
<223> OTHER INFORMATION: VL_CDR1 FOR CH-2

<400> SEQUENCE: 16

Ser Gly Gly Gly Ser Tyr Tyr Gly
1               5

<210> SEQ ID NO 17
<211> LENGTH: 7
<212> TYPE: PRT
<213> ORGANISM: Artificial Sequence
<220> FEATURE:
<223> OTHER INFORMATION: VL_CDR2 FOR CH-2

<400> SEQUENCE: 17

Asp Asn Thr Asn Arg Pro Ser
1               5

<210> SEQ ID NO 18
<211> LENGTH: 10
<212> TYPE: PRT
<213> ORGANISM: Artificial Sequence
<220> FEATURE:
<223> OTHER INFORMATION: VL_CDR3 FOR CH-2

<400> SEQUENCE: 18

Gly Ser Ala Asp Ser Ser Ala Glu Pro Val
1               5                   10

<210> SEQ ID NO 19
<211> LENGTH: 7
<212> TYPE: PRT
<213> ORGANISM: Artificial Sequence
<220> FEATURE:
<223> OTHER INFORMATION: VH_CDR1 FOR CH-3

<400> SEQUENCE: 19

Gly Phe Ser Phe Ser Asp Arg
1               5

<210> SEQ ID NO 20
<211> LENGTH: 6
<212> TYPE: PRT
<213> ORGANISM: Artificial Sequence
<220> FEATURE:
<223> OTHER INFORMATION: VH_CDR2 FOR CH-3

<400> SEQUENCE: 20

Arg Ser Asp Gly Ser Ser
1               5

<210> SEQ ID NO 21
<211> LENGTH: 14
<212> TYPE: PRT
<213> ORGANISM: Artificial Sequence
```

```
<220> FEATURE:
<223> OTHER INFORMATION: VH_CDR3 FOR CH-3

<400> SEQUENCE: 21

Asp Tyr Gly Asn Gly Gly Trp Ile Ala Gly Asp Ile Asp Ala
1               5                   10

<210> SEQ ID NO 22
<211> LENGTH: 8
<212> TYPE: PRT
<213> ORGANISM: Artificial Sequence
<220> FEATURE:
<223> OTHER INFORMATION: VL_CDR1 FOR CH-3

<400> SEQUENCE: 22

Ser Gly Asp Asn Ser Trp Tyr Gly
1               5

<210> SEQ ID NO 23
<211> LENGTH: 7
<212> TYPE: PRT
<213> ORGANISM: Artificial Sequence
<220> FEATURE:
<223> OTHER INFORMATION: VL_CDR2 FOR CH-3

<400> SEQUENCE: 23

Asp Ser Asp Gln Arg Pro Ser
1               5

<210> SEQ ID NO 24
<211> LENGTH: 13
<212> TYPE: PRT
<213> ORGANISM: Artificial Sequence
<220> FEATURE:
<223> OTHER INFORMATION: VL_CDR3 FOR CH-3

<400> SEQUENCE: 24

Cys Gly Ser Tyr Asp Ser Ser Ala Gly Tyr Ile Gly Ile
1               5                   10

<210> SEQ ID NO 25
<211> LENGTH: 22
<212> TYPE: PRT
<213> ORGANISM: Artificial Sequence
<220> FEATURE:
<223> OTHER INFORMATION: VH FOR HN-1

<400> SEQUENCE: 25

Gly Phe Thr Phe Ser Asp Arg Ser Asn Ala Gly Gly Tyr Gly Ala Ser
1               5                   10                  15

Tyr Asp Ala Ile Asp Ala
            20

<210> SEQ ID NO 26
<211> LENGTH: 25
<212> TYPE: PRT
<213> ORGANISM: Artificial Sequence
<220> FEATURE:
<223> OTHER INFORMATION: VL FOR HN-1

<400> SEQUENCE: 26

Ser Gly Ser Ser Arg Trp Tyr Ser Asn Asp Lys Arg Pro Ser Gly Ser
1               5                   10                  15

Gly Asp Ser Ser Ser Asn Pro Gly Ile
            20                  25
```

<210> SEQ ID NO 27
<211> LENGTH: 32
<212> TYPE: PRT
<213> ORGANISM: Artificial Sequence
<220> FEATURE:
<223> OTHER INFORMATION: VH FOR CH-1

<400> SEQUENCE: 27

Gly Phe Ser Phe Ser Gly Val Ser Ser Thr Gly Ser Gly Asp Ala Tyr
1               5                   10                  15

Gly Tyr Arg Ile Ser Gly Ser Trp Ser Tyr Gly Tyr Ser Ile Asp Ala
            20                  25                  30

<210> SEQ ID NO 28
<211> LENGTH: 26
<212> TYPE: PRT
<213> ORGANISM: Artificial Sequence
<220> FEATURE:
<223> OTHER INFORMATION: VL FOR CH-1

<400> SEQUENCE: 28

Ser Gly Gly Ser Asn Ser Tyr Tyr Gly Asp Asn Thr Asn Arg Pro Ser
1               5                   10                  15

Gly Ser Thr Asp Ser Ser Tyr Val Asp Ile
            20                  25

<210> SEQ ID NO 29
<211> LENGTH: 32
<212> TYPE: PRT
<213> ORGANISM: Artificial Sequence
<220> FEATURE:
<223> OTHER INFORMATION: VH FOR CH-2

<400> SEQUENCE: 29

Gly Phe Thr Phe Ser Ser Val Ser Asn Thr Gly Ser Gly Asp Ala Tyr
1               5                   10                  15

Gly Tyr Thr Ile Ser Gly Ser Trp Ser Tyr Gly Tyr Ser Ile Asp Ala
            20                  25                  30

<210> SEQ ID NO 30
<211> LENGTH: 25
<212> TYPE: PRT
<213> ORGANISM: Artificial Sequence
<220> FEATURE:
<223> OTHER INFORMATION: VL FOR CH-2

<400> SEQUENCE: 30

Ser Gly Gly Gly Ser Tyr Tyr Gly Asp Asn Thr Asn Arg Pro Ser Gly
1               5                   10                  15

Ser Ala Asp Ser Ser Ala Glu Pro Val
            20                  25

<210> SEQ ID NO 31
<211> LENGTH: 27
<212> TYPE: PRT
<213> ORGANISM: Artificial Sequence
<220> FEATURE:
<223> OTHER INFORMATION: VH FOR CH-3

<400> SEQUENCE: 31

Gly Phe Ser Phe Ser Asp Arg Arg Ser Asp Gly Ser Ser Asp Tyr Gly
1               5                   10                  15

Asn Gly Gly Trp Ile Ala Gly Asp Ile Asp Ala
            20                  25

<210> SEQ ID NO 32
<211> LENGTH: 28
<212> TYPE: PRT
<213> ORGANISM: Artificial Sequence
<220> FEATURE:
<223> OTHER INFORMATION: VL FOR CH-3

<400> SEQUENCE: 32

Ser Gly Asp Asn Ser Trp Tyr Gly Asp Ser Asp Gln Arg Pro Ser Cys
1               5                   10                  15

Gly Ser Tyr Asp Ser Ser Ala Gly Tyr Ile Gly Ile
            20                  25

<210> SEQ ID NO 33
<211> LENGTH: 723
<212> TYPE: DNA
<213> ORGANISM: artificial
<220> FEATURE:
<223> OTHER INFORMATION: HN-1

<400> SEQUENCE: 33

```
ctgactcagc cgtcctcggt gtcagcgaac ccgggagaaa ccgtcaagat cacctgctcc      60
gggagtagca gatggtacgg ctggttccag cagaagtctc ctggcagtgc ccctgtcact     120
ctgatctata gcaacgacaa gagaccctcg gacatccctt cacgattctc cggttccaca     180
tccggctcca caagcacatt aaccatcact ggggtccaag ccgacgacga ggctgtctat     240
tactgtggga gtgagacag cagcagtaat cctggtatat ttggggccgg acaaccctg      300
accgtcctag gtcagtcctc tagatcttcc ggcggtggtg gcagctccgg tggtggcggt     360
tccgccgtga cgttggacga gtccgggggc ggcctccaga cgcccggagg agggctcagc     420
ctcgtctgca aggcctccgg gttcaccttc agtgaccgtg gcatgcactg ggtgcgacag     480
gcgcccggca aggggttgga actcgtcgca agtattagca acgctggtgg ttacacaaac     540
tacgggtcgg cggtgaaggg ccgtgccacc atctcgaggg acaacgggca gagcacactg     600
aggctgcagc tgaacaacct cagggctgag gacaccgcca cctactactg cgccagaggt     660
gctagttatg atgcaatcga cgcatggggc cacgggaccg aagtcatcgt ctcctccact     720
agt                                                                  723
```

<210> SEQ ID NO 34
<211> LENGTH: 753
<212> TYPE: DNA
<213> ORGANISM: artificial sequence
<220> FEATURE:
<223> OTHER INFORMATION: CH-1

<400> SEQUENCE: 34

```
ctgactcagc cgtcctcggt gtcagcaaac ccaggagaaa ccgtcgagat cacctgctcc      60
gggggtagca acagctacta tggctggtac cagcagaagt ctcctggcag tgcccctgtc     120
actgtgatct atgacaacac caacagaccc tcgaacatcc cttcacgatt ctccggttcc     180
acatccggct ccacaagcac attaaccatc actggggtcc aagccgacga cgaggctgtc     240
tattactgtg ggagcacgga cagcagctat gttgatatat ttggggccgg acaaccctg      300
accgtcctag gtcagtcctc tagatcttcc ggcggtggtg gcagctccgg tggtggcggt     360
tccgccgtga cgttggacga gtccgggggc ggcctccaga cgcccggagg agcgctcagc     420
ctcgtctgca aggcctccgg gttctccttc agcggcgtca acatgcactg ggtgcgccag     480
```

| | |
|---|---|
| gctccaggca aggggttgga atacgtcgct caaattagca gcactggtag tggcacagga | 540 |
| tacgggtcgg cggtgcaggg ccgtgccacc atctcgaggg acaacgggca gagcacagtg | 600 |
| aggctgcagc tgaacaacct cagggctgag acaccggca tctactactg tgccaaagat | 660 |
| gcttacggtt atcgtattag tggtagttgg agttatggtt acagtatcga cgcatggggc | 720 |
| cacgggaccg aagtcatcgt ctcctccact agt | 753 |

<210> SEQ ID NO 35
<211> LENGTH: 750
<212> TYPE: DNA
<213> ORGANISM: artificial sequence
<220> FEATURE:
<223> OTHER INFORMATION: CH-2

<400> SEQUENCE: 35

| | |
|---|---|
| ctgactcagc cgtcctcggt gtcagcgaac ccgggagaaa ccgtcaagat cacctgctcc | 60 |
| gggggtggca gctactatgg ctggtaccag cagaaggcac ctggcagtgc ccctgtcact | 120 |
| ctgatctatg acaacaccaa cagaccctcg gacatcccctt cacgattctc cggttccaca | 180 |
| tctggctcca caagcacatt aaccatcact ggggtccaag ccgacgacga ggctgtctat | 240 |
| ttctgtggga gtgcagacag cagtgctgag cctgtatttg ggccgggac aaccctgacc | 300 |
| gtcctaggtc agtcctctag atcttccggc ggtggtggca gctccggtgg tggcggttcc | 360 |
| gccgtgacgt tggacgagtc cggggggcgg ctccagacgc ccgaggagc gctcagcctc | 420 |
| gtctgcaagg cctccgggtt caccttcagc agcgtcaaca tgcactgggt gcgccaggct | 480 |
| ccaggcaagg ggttggaata cgtcgctcaa attagcaaca ctggtagtgg tacaggctac | 540 |
| ggggcggcgg tgcagggccg tgccaccatc tcgagggaca cgggcagag cacagtgagg | 600 |
| ctgcagctga caaacctcag ggctgaggac accggcatct actactgtgc caaagatgct | 660 |
| tacggttata ctattagtgg tagttggagt tatggttaca gtatcgacgc atggggccac | 720 |
| gggaccgaag tcatcgtctc tccactagt | 750 |

<210> SEQ ID NO 36
<211> LENGTH: 741
<212> TYPE: DNA
<213> ORGANISM: artificial sequence
<220> FEATURE:
<223> OTHER INFORMATION: CH-3

<400> SEQUENCE: 36

| | |
|---|---|
| ctgactcagc cgtcctcggt gtcagcaaac ccaggagaaa ccgtcgagat cacctgctcc | 60 |
| gggggataaca gctggtatgg ctggtatcag cagaagtcac ctggcagtgc ccctgtcact | 120 |
| ctgatctatg acagcgacca gagaccctcg ggcatcccct cacgattctc cggttccaca | 180 |
| tctgactcca cgggcacatt aaccatcact ggggtccaag tcgacgacga ggctgtctat | 240 |
| tactgtggga gctacgacag cagtgctggt tatattggta tatttggggc cgggacaacc | 300 |
| ctgaccgtcc taggtcagtc ctctagatct tccggcggtg gtggcagctc cggtggtggc | 360 |
| ggttccgccg tgacgttgga cgagtccggg ggcggcctcc agacgcccgg aggagcgctc | 420 |
| agcctcgtct gcaaggcctc cgggttctcc ttcagtgacc gtgcatgca ctgggtgcga | 480 |
| caggcacccg gcaagggggct ggagtgggtc gcgggtatta gaagtgatgg tagtagcaca | 540 |
| tactacgggg cggcggtgaa gggccgtgcc accatctcga gggacaacgg gcagagcaca | 600 |
| gtgaggatgc agctgaacaa cctcaggggct gaggacaccg gcacctacta ctgcgccaga | 660 |
| gattatggca atggtggttg gattgctggt gacatcgacg catggggcca cgggaccgaa | 720 | gtcatcgtct cctccactag t                                            741

<210> SEQ ID NO 37
<211> LENGTH: 37
<212> TYPE: DNA
<213> ORGANISM: Artificial Sequence
<220> FEATURE:
<223> OTHER INFORMATION: Primer HSCK1-F

<400> SEQUENCE: 37
gggcccaggc ggccgagctc cagatgaccc agtctcc                           37

<210> SEQ ID NO 38
<211> LENGTH: 37
<212> TYPE: DNA
<213> ORGANISM: Artificial Sequence
<220> FEATURE:
<223> OTHER INFORMATION: Primer HSCK24-F

<400> SEQUENCE: 38
gggcccaggc ggccgagctc gtgatgacyc agtctcc                           37

<210> SEQ ID NO 39
<211> LENGTH: 37
<212> TYPE: DNA
<213> ORGANISM: Artificial Sequence
<220> FEATURE:
<223> OTHER INFORMATION: Primer HSCK3-F

<400> SEQUENCE: 39
gggcccaggc ggccgagctc gtgwtgacrc agtctcc                           37

<210> SEQ ID NO 40
<211> LENGTH: 37
<212> TYPE: DNA
<213> ORGANISM: Artificial Sequence
<220> FEATURE:
<223> OTHER INFORMATION: Primer HSCK5-F

<400> SEQUENCE: 40
gggcccaggc ggccgagctc acactcacgc agtctcc                           37

<210> SEQ ID NO 41
<211> LENGTH: 42
<212> TYPE: DNA
<213> ORGANISM: Artificial Sequence
<220> FEATURE:
<223> OTHER INFORMATION: Primer HSCJK14o-B

<400> SEQUENCE: 41
ggaagatcta gaggaaccac ctttgatytc caccttggtc cc                     42

<210> SEQ ID NO 42
<211> LENGTH: 42
<212> TYPE: DNA
<213> ORGANISM: Artificial Sequence
<220> FEATURE:
<223> OTHER INFORMATION: Primer HSCJK2o-B

<400> SEQUENCE: 42
ggaagatcta gaggaaccac ctttgatctc cagcttggtc cc                     42

<210> SEQ ID NO 43
<211> LENGTH: 42
<212> TYPE: DNA

```
<213> ORGANISM: Artificial Sequence
<220> FEATURE:
<223> OTHER INFORMATION: Primer HSCJK3o-B

<400> SEQUENCE: 43
ggaagatcta gaggaaccac ctttgatatc cactttggtc cc                    42

<210> SEQ ID NO 44
<211> LENGTH: 42
<212> TYPE: DNA
<213> ORGANISM: Artificial Sequence
<220> FEATURE:
<223> OTHER INFORMATION: Primer HSCJK5o-B

<400> SEQUENCE: 44
ggaagatcta gaggaaccac ctttaatctc cagtcgtgtc cc                    42

<210> SEQ ID NO 45
<211> LENGTH: 40
<212> TYPE: DNA
<213> ORGANISM: Artificial Sequence
<220> FEATURE:
<223> OTHER INFORMATION: Primer HSCLam1a

<400> SEQUENCE: 45
gggcccaggc ggccgagctc gtgbtgacgc agccgccctc                       40

<210> SEQ ID NO 46
<211> LENGTH: 40
<212> TYPE: DNA
<213> ORGANISM: Artificial Sequence
<220> FEATURE:
<223> OTHER INFORMATION: Primer HSCLam1b

<400> SEQUENCE: 46
gggcccaggc ggccgagctc gtgctgactc agccaccctc                       40

<210> SEQ ID NO 47
<211> LENGTH: 43
<212> TYPE: DNA
<213> ORGANISM: Artificial Sequence
<220> FEATURE:
<223> OTHER INFORMATION: Primer HSCLam2

<400> SEQUENCE: 47
gggcccaggc ggccgagctc gccctgactc agcctccctc cgt                   43

<210> SEQ ID NO 48
<211> LENGTH: 46
<212> TYPE: DNA
<213> ORGANISM: Artificial Sequence
<220> FEATURE:
<223> OTHER INFORMATION: Primer HSCLam3

<400> SEQUENCE: 48
gggcccaggc ggccgagctc gagctgactc agccaccctc agtgtc                46

<210> SEQ ID NO 49
<211> LENGTH: 40
<212> TYPE: DNA
<213> ORGANISM: Artificial Sequence
<220> FEATURE:
<223> OTHER INFORMATION: Primer HSCLam4

<400> SEQUENCE: 49
gggcccaggc ggccgagctc gtgctgactc aatcgccctc                       40
```

<210> SEQ ID NO 50
<211> LENGTH: 40
<212> TYPE: DNA
<213> ORGANISM: Artificial Sequence
<220> FEATURE:
<223> OTHER INFORMATION: Primer HSCLam6

<400> SEQUENCE: 50
gggcccaggc ggccgagctc atgctgactc agccccactc         40

<210> SEQ ID NO 51
<211> LENGTH: 40
<212> TYPE: DNA
<213> ORGANISM: Artificial Sequence
<220> FEATURE:
<223> OTHER INFORMATION: Primer HSCLam78

<400> SEQUENCE: 51
gggcccaggc ggccgagctc gtggtgacyc aggagccmtc         40

<210> SEQ ID NO 52
<211> LENGTH: 40
<212> TYPE: DNA
<213> ORGANISM: Artificial Sequence
<220> FEATURE:
<223> OTHER INFORMATION: Primer HSCLam9

<400> SEQUENCE: 52
gggcccaggc ggccgagctc gtgctgactc agccaccttc         40

<210> SEQ ID NO 53
<211> LENGTH: 45
<212> TYPE: DNA
<213> ORGANISM: Artificial Sequence
<220> FEATURE:
<223> OTHER INFORMATION: Primer HSCJLam1236

<400> SEQUENCE: 53
ggaagatcta gaggaaccac cgcctaggac ggtcascttg gtscc    45

<210> SEQ ID NO 54
<211> LENGTH: 45
<212> TYPE: DNA
<213> ORGANISM: Artificial Sequence
<220> FEATURE:
<223> OTHER INFORMATION: Primer HSCJLam57

<400> SEQUENCE: 54
ggaagatcta gaggaaccac cgccgaggac ggtcagctsg gtscc    45

<210> SEQ ID NO 55
<211> LENGTH: 77
<212> TYPE: DNA
<213> ORGANISM: Artificial Sequence
<220> FEATURE:
<223> OTHER INFORMATION: Primer HSCVH1-FL

<400> SEQUENCE: 55
ggtggttcct ctagatcttc ctcctctggt ggcggtggct cgggcggtgg tgggcaggtg    60
cagctggtgc agtctgg                                                   77

<210> SEQ ID NO 56
<211> LENGTH: 77
<212> TYPE: DNA

```
<213> ORGANISM: Artificial Sequence
<220> FEATURE:
<223> OTHER INFORMATION: Primer HSCVH2-FL

<400> SEQUENCE: 56
ggtggttcct ctagatcttc ctcctctggt ggcggtggct cgggcggtgg tgggcagatc      60
accttgaagg agtctgg                                                    77

<210> SEQ ID NO 57
<211> LENGTH: 77
<212> TYPE: DNA
<213> ORGANISM: Artificial Sequence
<220> FEATURE:
<223> OTHER INFORMATION: Primer HSCVH35-FL

<400> SEQUENCE: 57
ggtggttcct ctagatcttc ctcctctggt ggcggtggct cgggcggtgg tggggaggtg      60
cagctggtgs agtctgg                                                    77

<210> SEQ ID NO 58
<211> LENGTH: 76
<212> TYPE: DNA
<213> ORGANISM: Artificial Sequence
<220> FEATURE:
<223> OTHER INFORMATION: Primer HSCVH3a-FL

<400> SEQUENCE: 58
ggtggttcct ctagatcttc ctcctctggt ggcggtggct cgggcggtgg tggggaggtg      60
cagctgktgg agtctg                                                     76

<210> SEQ ID NO 59
<211> LENGTH: 77
<212> TYPE: DNA
<213> ORGANISM: Artificial Sequence
<220> FEATURE:
<223> OTHER INFORMATION: Primer HSCVH4-FL

<400> SEQUENCE: 59
ggtggttcct ctagatcttc ctcctctggt ggcggtggct cgggcggtgg tgggcaggtg      60
cagctgcagg agtcggg                                                    77

<210> SEQ ID NO 60
<211> LENGTH: 77
<212> TYPE: DNA
<213> ORGANISM: Artificial Sequence
<220> FEATURE:
<223> OTHER INFORMATION: Primer HSCVH4a-FL

<400> SEQUENCE: 60
ggtggttcct ctagatcttc ctcctctggt ggcggtggct cgggcggtgg tgggcaggtg      60
cagctacagc agtgggg                                                    77

<210> SEQ ID NO 61
<211> LENGTH: 46
<212> TYPE: DNA
<213> ORGANISM: Artificial Sequence
<220> FEATURE:
<223> OTHER INFORMATION: Primer HSCVH4a-FL

<400> SEQUENCE: 61
cctggccggc ctggccacta gtgaccgatg ggcccttggt ggargc                    46
```

```
<210> SEQ ID NO 62
<211> LENGTH: 46
<212> TYPE: DNA
<213> ORGANISM: Artificial Sequence
<220> FEATURE:
<223> OTHER INFORMATION: Primer HSCM-B

<400> SEQUENCE: 62
cctggccggc ctggccacta gtaagggttg gggcggatgc actccc        46

<210> SEQ ID NO 63
<211> LENGTH: 41
<212> TYPE: DNA
<213> ORGANISM: Artificial Sequence
<220> FEATURE:
<223> OTHER INFORMATION: Primer RSC-F

<400> SEQUENCE: 63
gaggaggagg aggaggaggc ggggcccagg cggccgagct c             41

<210> SEQ ID NO 64
<211> LENGTH: 41
<212> TYPE: DNA
<213> ORGANISM: Artificial Sequence
<220> FEATURE:
<223> OTHER INFORMATION: Primer RSC-B

<400> SEQUENCE: 64
gaggaggagg aggaggagcc tggccggcct ggccactagt g             41

<210> SEQ ID NO 65
<211> LENGTH: 38
<212> TYPE: DNA
<213> ORGANISM: Artificial Sequence
<220> FEATURE:
<223> OTHER INFORMATION: Primer CSCVK

<400> SEQUENCE: 65
gtggcccagg cggccctgac tcagccgtcc tcggtgtc                 38

<210> SEQ ID NO 66
<211> LENGTH: 34
<212> TYPE: DNA
<213> ORGANISM: Artificial Sequence
<220> FEATURE:
<223> OTHER INFORMATION: Primer CKJo-B

<400> SEQUENCE: 66
ggaagatcta gaggactgac ctaggacggt cagg                     34

<210> SEQ ID NO 67
<211> LENGTH: 72
<212> TYPE: DNA
<213> ORGANISM: Artificial Sequence
<220> FEATURE:
<223> OTHER INFORMATION: Primer CSCVHo-FL

<400> SEQUENCE: 67
ggtcagtcct ctagatcttc cggcggtggt ggcagctccg gtggtggcgg    50
ttccgccgtg acgttggacg cg                                  72

<210> SEQ ID NO 68
<211> LENGTH: 44
<212> TYPE: DNA
<213> ORGANISM: Artificial Sequence
<220> FEATURE:
```

```
<223> OTHER INFORMATION: Primer CSCG-B

<400> SEQUENCE: 68
ctggccggcc tggccactag tggaggagac gatgacttcg gtcc                    44

<210> SEQ ID NO 69
<211> LENGTH: 42
<212> TYPE: DNA
<213> ORGANISM: Artificial Sequence
<220> FEATURE:
<223> OTHER INFORMATION: Primer CSC-F

<400> SEQUENCE: 69
gaggaggagg aggaggaggt ggcccaggcg gccctgactc ag                      42

<210> SEQ ID NO 70
<211> LENGTH: 47
<212> TYPE: DNA
<213> ORGANISM: Artificial Sequence
<220> FEATURE:
<223> OTHER INFORMATION: Primer CSC-B

<400> SEQUENCE: 70
gaggaggagg aggaggagga gctggccggc ctggccacta gtggagg                 47
```

MONOCLONAL ANTIBODY SPECIFICALLY BINDING TO CCSP-2 AND USE THEREOF

CROSS REFERENCE TO RELATED APPLICATIONS

This application is a 371 of PCT/KR2020/001370 filed on Jan. 29, 2020, which claims the benefit of priority from Korean Patent Application No. 10-2019-0011172 filed on Jan. 29, 2019, the contents of each of which are incorporated herein by reference in their entirety.

TECHNICAL FIELD

The present invention relates to a monoclonal antibody specifically binding to an EGF2 domain of human colon cancer secreted protein-2 (CCSP-2), or an antigen-binding fragment thereof.

BACKGROUND ART

The large intestine belongs to the digestive system and is an organ located between the small intestine and the anus. The total length is approximately 1.5 meters on average, and classified into the cecum, the ascending colon, the transverse colon, the descending colon, the sigmoid colon and the rectum from the right. Colorectal cancer is a malignant tumor that occurs in the colon and rectum, and malignant tumor cells (cancer cells) mainly arise from epithelial cells. Depending on a region where cancer occurs, cancer that occurs in the colon is called colon cancer, cancer that occurs in the rectum is called rectal cancer, and these are collectively called colorectal cancer.

According to national cancer registration statistics, a total of 28,112 cases of colorectal cancer occurred in 2011, accounting for 12.9% of the total cancer incidence (218,017 cases), ranking $3^{rd}$ in cancer incidence and $4^{th}$ in cancer mortality.

Another reason for a continuous increase in colorectal cancer mortality is that there are few initial symptoms of colorectal cancer, and therefore, the early detection rate of colorectal cancer in Korea is low as less than 10%. Many colorectal cancer patients are diagnosed with metastatic colorectal cancer in stages 3 and 4, when metastasis to other organs begins. The survival rate of Stage 3 colorectal cancer is quite low, 28%, and the survival rate of Stage 4 colorectal cancer is 6%, which is lower than the survival rate of Stage 3 colorectal cancer. Accordingly, the early diagnosis of colorectal cancer is very important.

Currently, the most prevalently used methods for colorectal cancer diagnosis are a double contrast barium-enema and colonoscopy. A double contrast barium-enema is an examination method of inserting a small tube through the anus after cleaning the large intestine to inject a contrast agent called barium, coating the wall of the large intestine with a thin layer of barium while expanding the large intestine by injecting air, and taking images using an X-ray fluoroscope. Advantages of this method are identification of the overall contour and shape of the large intestine, easy identification of the overall location of colorectal cancer, and easy testing for the changes in the large intestinal wall such as inflammatory or ischemic changes and the distal end of the small intestine. However, there are disadvantages that tissue cannot be obtained with testing, and accuracy for small polyps is inferior to colonoscopy.

As a testing method for directly examining the large intestine with light and a flexible tube, colonoscopy is the most accurate method for diagnosing a colorectal disease, and this is because a doctor can directly observe the area of bleeding and the surface of a lesion, and determine the condition of tissue. A biopsy is also possible at the same time as an endoscopy, and when a conscious sedation endoscopy is performed while a patient is sleeping by intravenously injecting a sedative acting only for a short period of time, testing can be done without discomfort.

Colonoscopy is the best diagnostic tool for finding colorectal cancer, but the frequency at which polyps missed in the testing are detected as having advanced to cancer in the patient's next test is high. Since polyps larger than 1 cm have a relatively and significantly increasing possibility of progression to cancer over time, it is necessary to improve the technology so as not to miss a small polyp during an endoscopy, and to attempt to avoid missing lesions behind flexures and mucosal folds with sufficient margin during withdrawal inspection. As one of these attempts, research is being conducted on the development of a biomarker and a marker, which are used in molecular imaging, to improve a tumor detection rate.

Meanwhile, a colon cancer secreted protein (e.g., CCSP-2) is a colorectal cancer-specific marker (biomarker), and information on the gene encoding the same is well known in the related art. For example, the CCSP-2 may be human CCSP-2, and the information on the human CCSP-2 protein is registered at National Center for Biotechnology Information (NCBI) under Accession No. AAT77225.1, and the information on a gene encoding the same is registered at NCBI under Accession No. AY572972.1. The function and role of the CCSP-2 are not well known, but at the RNA level, it is known that the average expression level thereof in colorectal cancer cells and/or tissue is 78-fold higher than in normal tissue (colorectal cancer cell-free tissue). In addition, the CCSP-2 is a secretory protein and an extracellular matrix (ECM) protein, which is increased in colorectal cancer-specific expression, and has advantages of labeling colorectal cancer tissue through targeting CCSP-2 protein accumulated in colorectal cancer tissue as well as diagnosis of colorectal cancer using blood. Accordingly, when the expression and/or expression level of CCSP-2 is(are) measured at the gene and/or protein level(s), the presence of colorectal cancer and/or the degree of progression of colorectal cancer may be accurately and easily confirmed.

There is a problem that a currently commercially available antibody specifically binding to CCSP-2 has low specificity, and thus binds to approximately 50% normal cells (or tissue) rather than colorectal cancer cells (or tissue) for labeling.

In this regard, the inventors developed a peptide specifically binding to CCSP-2, confirmed the effect of specifically detecting CCSP-2 at the protein level, and proved that colorectal cancer and/or colorectal cancer cells and/or tissue can be detected, which is disclosed in Korean Patent Application Publication No. 10-2018-0060184.

While continuing research on the technology of specifically detecting the CCSP-2, the inventors developed a monoclonal antibody specifically binding to the EGF2 domain of CCSP-2, and confirmed that the antibody is significantly improved in affinity and particularly more improved in specificity, compared with a conventional peptide specifically binding to CCSP-2, and thus the present invention was completed.

DISCLOSURE

Technical Problem

The present invention is directed to providing a monoclonal antibody specifically binding to colon cancer secreted protein-2 (CCSP-2), or an antigen-binding fragment thereof.

The present invention is also directed to providing a polynucleotide encoding the monoclonal antibody or an antigen-binding fragment thereof, an expression vector including the polynucleotide and a transformant into which the vector is introduced.

The present invention is also directed to providing a composition for diagnosing cancer, which includes the monoclonal antibody or the antigen-binding fragment thereof.

The present invention is also directed to providing a kit for diagnosing cancer, which includes the monoclonal antibody or the antigen-binding fragment thereof.

The present invention is also directed to providing a method of providing information for cancer diagnosis, which includes detecting a CCSP-2 protein in a biological sample isolated from a subject suspected of having cancer using the monoclonal antibody or the antigen-binding fragment thereof through an antigen-antibody reaction.

Technical Solution

To achieve the above-described objects, the present invention provides a monoclonal antibody specifically binding to the EGF2 domain of human CCSP-2, which includes a heavy chain variable region and a light chain variable region selected from the group consisting of 1) to 4) below, or an antigen-binding fragment thereof:

1) a heavy chain variable region including a CDR1 region represented by SEQ ID NO: 1, a CDR2 region represented by SEQ ID NO: 2 and a CDR3 region represented by SEQ ID NO: 3, and a light chain variable region including a CDR1 region represented by SEQ ID NO: 4, a CDR2 region represented by SEQ ID NO: 5 and a CDR3 region SEQ ID NO: 6;

2) a heavy chain variable region including a CDR1 region represented by SEQ ID NO: 7, a CDR2 region represented by SEQ ID NO: 8 and a CDR3 region represented by SEQ ID NO: 9, and a light chain variable region including a CDR1 region represented by SEQ ID NO: 10, a CDR2 region represented by SEQ ID NO: 11 and a CDR3 region represented by SEQ ID NO: 12;

3) a heavy chain variable region including a CDR1 region represented by SEQ ID NO: 13, a CDR2 region represented by SEQ ID NO: 14 and a CDR3 region represented by SEQ ID NO: 15, and a light chain variable region including a CDR1 region represented by SEQ ID NO: 16, a CDR2 region represented by SEQ JD NO: 17 and a CDR3 region represented by SEQ ID NO: 18; and 4) a heavy chain variable region including a CDR1 region represented by SEQ ID NO: 19, a CDR2 region represented by SEQ ID NO: 20 and a CDR3 region represented by SEQ ID NO: 21, and a light chain variable region including a CDR1 region represented by SEQ ID NO: 22, a CDR2 region represented by SEQ ID NO: 23 and a CDR3 region represented by SEQ ID NO: 24.

In one embodiment of the present invention, the antigen-binding fragment may be selected from the group consisting of Fab, Fab', F(ab')2, scFv, Fv, dsFv, a diabody, Fd and Fd'.

In one embodiment of the present invention, the monoclonal antibody or the antigen-binding fragment thereof may include a heavy chain variable region and a light chain variable region, which are selected from the group consisting of a heavy chain variable region including a polypeptide sequence represented by SEQ ID NO: 25 and a light chain variable region including a polypeptide sequence represented by SEQ ID NO: 26; a heavy chain variable region including a polypeptide sequence represented by SEQ ID NO: 27 and a light chain variable region including a polypeptide sequence represented by SEQ ID NO: 28; a heavy chain variable region including a polypeptide sequence represented by SEQ ID NO: 29 and a light chain variable region including a polypeptide sequence represented by SEQ ID NO: 30; and a heavy chain variable region including a polypeptide sequence represented by SEQ ID NO: 31 and a light chain variable region including a polypeptide sequence represented by SEQ ID NO: 32.

The present invention also provides a polynucleotide encoding the monoclonal antibody, or an antigen-binding fragment thereof.

The present invention also provides an expression vector including the polynucleotide.

The present invention also provides a transformant into which the expression vector is introduced, excluding a human.

The present invention also provides a composition for diagnosing cancer, which includes the monoclonal antibody or the antigen-binding fragment thereof.

In one embodiment of the present invention, the cancer may be selected from the group consisting of esophageal cancer, gastric cancer, colorectal cancer, rectal cancer, oral cancer, pharyngeal cancer, laryngeal cancer, lung cancer, colon cancer, breast cancer, cervical cancer, endometrial cancer, ovarian cancer, prostate cancer, testicular cancer, bladder cancer, kidney cancer, liver cancer, pancreatic cancer, bone cancer, connective tissue cancer, skin cancer, brain cancer, thyroid cancer, leukemia, Hodgkin's disease, soft tissue sarcoma, lymphoma and multiple myeloma hematologic cancer.

The present invention also provides a kit for diagnosing cancer, which includes the composition.

The present invention also provides a method of providing information for cancer diagnosis, which includes detecting CCSP-2 protein in a biological sample isolated from a subject suspected of having cancer using the monoclonal antibody or the antigen-binding fragment thereof through an antigen-antibody reaction.

Advantageous Effects

As a monoclonal antibody of the present invention or an antigen-binding fragment thereof specifically binds to the EGF2 domain of CCSP-2, compared with a conventional peptide specifically binding to CCSP-2, affinity can be significantly improved, and compared with a conventional antibody against CCSP-2, specificity can be more improved. Accordingly, CCSP-2 is specifically detected at the protein level and thus enables accurate diagnosis in the future.

MODES OF THE INVENTION

Figure 1:
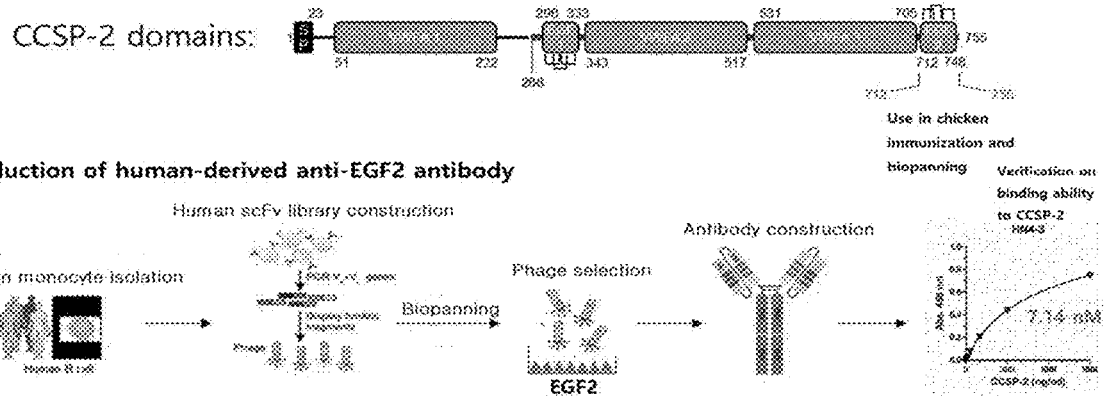
FIG. 1 is a schematic diagram illustrating the strategy of cloning a variable region of a scFv antibody according to one embodiment of the present invention.
Figure 1:
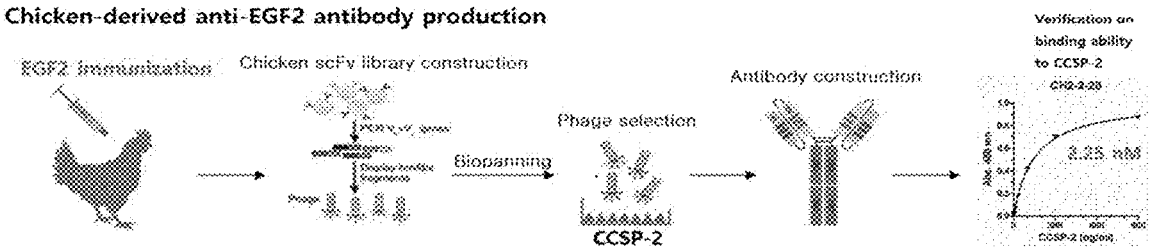

Hereinafter, the present invention will be described in detail.

The present invention provides a monoclonal antibody specifically binding to the EGF2 domain of human colon cancer secreted protein-2 (CCSP-2), or an antigen-binding fragment. The CCSP-2 is specific for colorectal cancer (e.g., expressed specifically in colorectal cancer).

The inventors identified antibodies specifically recognizing CCSP-2, and the amino acid sequence of a heavy chain variable region thereof, the amino acid sequence of a light chain variable region thereof and coding nucleotide sequences thereof.

In addition, according to one exemplary embodiment of the present invention, colorectal cancer and/or colorectal cancer cells and/or tissue can be accurately diagnosed by specifically detecting CCSP-2 by providing a monoclonal antibody or an antigen-binding fragment thereof specifically binding to CCSP-2, and particularly, it may be effectively applied to the endoscopic diagnosis of colorectal cancer by visualizing colorectal tissue with the antibody conjugated with a visible labeling material.

The term "antibody" used herein refers to a protein molecule serving as a receptor specifically recognizing an antigen, which includes an immunoglobulin molecule immunologically having reactivity to a specific antigen, and includes a polyclonal antibody, a monoclonal antibody, and an antigen-binding fragment (antibody fragment) of an antibody molecule as well as a complete antibody form. In addition, the term includes a chimeric antibody, a humanized antibody, a bivalent or bispecific molecule (e.g., bispecific antibody), a diabody, a triabody, and a tetrabody.

The term "complete antibody" has a structure having two full-length light chains and two full-length heavy chains, in which each light chain is connected with a heavy chain by a disulfide bond. The complete antibody includes IgA, IgD, IgE, IgM and IgG, in which IgG has subtypes, for example, IgG1, IgG2, IgG3 and IgG4.

The term "antigen-binding fragment of an antibody" used herein refers to a fragment that retains an antigen-antibody binding function in a complete antibody molecule, and includes Fab, Fab', F(ab')2, scFv, Fv, dsFv, a diabody, Fd and Fd'. The Fab has a structure having light and heavy chain variable regions, and a constant region of the light chain and the first constant region (CH1 domain) of the heavy chain, and has one antigen-binding site. An Fab' is distinguished from Fab in that there is a hinge region having one or more cysteine residues at the C terminus of the CH1 domain of the heavy chain. An F(ab')2 antibody is generated by forming a disulfide bond between cysteine residues of the hinge region of Fab'. A variable fragment (Fv) refers to the smallest antibody fragment only having a heavy chain variable region and a light chain variable region. Double chain Fv (dsFv) is formed by connecting a heavy chain variable region and a light chain variable region using a disulfide bond, and single chain Fv (scFv) generally has the same structure as a dimer such as dsFv since a heavy chain variable region is connected with a light chain variable region by a covalent bond using a peptide linker, or may be directly connected to the C-terminus. A diabody is a complex of two or more polypeptide chains or proteins, and refers to a complex including at least one VL domain and at least one VH domain or fragments thereof, and having both domains in a single polypeptide chain. In one embodiment, the diabody includes a molecule including an Fc or hinge-Fc domain. The polypeptide chains of such a complex may be the same or different, in other words, the diabody may be a mono polymer or a hetero polymer.

The antigen-binding fragment may be obtained using proteases (e.g., Fab may be obtained by restriction of a complete antibody by papain, and a $F(ab')_2$ fragment may be obtained by cleavage by a pepsin), and preferably is manufactured using gene recombination technology.

The term "heavy chain" used herein refers to both a full-length heavy chain which consists of a variable region domain VH and three constant region domains CH1, CH2 and CH3, and a fragment thereof, which includes an amino acid sequence having a sufficient variable region sequence imparting specificity to an antigen. In addition, the term "light chain" used herein refers to both a full-length light chain which consists of a variable region domain VL and a constant region domain. CL, or a fragment thereof, which includes an amino acid sequence having a sufficient variable region sequence imparting specificity to an antigen.

The term "monoclonal antibody" used herein refers to an antibody molecule of single molecular composition obtained from substantially the same antibody population, and exhibits single binding specificity and affinity for a specific epitope. Typically, an immunoglobulin has a heavy chain and a light chain, in which each of the heavy chain and the light chain includes a constant region and a variable region (these regions are also known as domains). The variable regions of the light chain and heavy chain includes three variable regions called complementarity-determining regions (hereinafter, referred to as "CDRs") and four framework regions (FRs). The CDRs mainly serve to bind to an epitope of an antigen. The CDRs of each chain are typically called CDR1, CDR2 and CDR3 sequentially from the N-terminus, and also distinguished by a chain in which a specific CDR is located.

The term "complementarity determining region (CDR)" refers to the amino acid sequence of a variable region (hypervariable region) of an immunoglobulin heavy or light chain (Kabat et al. Sequences of Proteins of Immunological Interest, 4$^{th}$ Ed., U.S. Department of Health and Human Services, National Institutes of Health (1987)). Three CDRs are included in each heavy chain (CDR1-11, CDRH2 and CDRH3) and each light chain (CDRL1, CDRL2 and CDRL3) and provide major contact residues for an antibody to bind to an antigen or epitope.

Meanwhile, the monoclonal antibody may be in the form of a chimeric antibody or humanized antibody which has reduced immunogenicity to be applied to a human as described above.

The term "chimeric antibody" is an antibody formed by combining a variable region of a heterogeneous antibody which is derived from a mouse or chicken and a constant region of a human antibody through DNA recombination technology, and the immune reaction of the chimeric antibody is considerably improved compared with a heterogeneous antibody derived from a mouse or chicken, and thus can be used clinically.

The term "humanized antibody" used herein refers to an antibody formed by transplanting all or a part of the CDR sequence of a heterogeneous monoclonal antibody derived from a mouse or chicken into a human antibody, a humanized variable region may be formed by recombining CDRs of a chicken or mouse monoclonal antibody with a human antibody-derived FR, and the human antibody may be formed by recombining the variable region with a constant region of a preferred human antibody, but the present invention is not limited thereto. In addition, since the affinity of a humanized antibody is decreased when only the chicken or mouse-derived CDRs are inserted, the affinity may be improved by substituting an FR amino acid residue, which may be considered to affect the three-dimensional structure of a CDR, with an amino acid of a chicken or mouse antibody, but the present invention is not limited thereto.

The term "monoclonal antibody specifically binding to the EGF2 domain of colon cancer secreted protein-2 (CCSP-2)" refers to an antibody capable of specifically binding to CCSP-2, and may be interchangeably used with an anti-CCSP-2 antibody. The monoclonal antibody specifically binding to the CCSP-2 protein may be, without limitation, any monoclonal antibody that binds to CCSP-2 to inhibit the biological activity of CCSP-2.

In addition, the form of monoclonal antibody may include both of a complete antibody and an antigen-binding fragment as described above, and may be a chimeric antibody or a humanized antibody, but the present invention is not limited thereto. In addition, the monoclonal antibody of the present invention may specifically bind to the EGF2 domain of CCSP-2 to inhibit signaling by CCSP-2, resulting in suppression of biological activity, and thus may be effectively used for prevention or treatment of a disease such as cancer mediated by CCSP-2. In addition, since CCSP-2 overexpression is reported as a specific phenomenon in cancer, and the antibody of the present invention capable of specifically binding to CCSP-2 has diagnosis ability with high sensitivity and specificity in the diagnosis of cancer, the antibody may be effectively used in diagnosis of cancer. In one embodiment of the present invention, an antigen-binding fragment specifically binding to CCSP-2 of the present invention was formed using the EGF2 site of CCSP-2 as an antigen protein.

The monoclonal antibody specifically binding to the EGF2 domain of the human CCSP-2, or an antigen-binding fragment thereof may include any one pair of a heavy chain variable region and a light chain variable region selected from the group consisting of 1) to 4) below, but the present invention is not limited thereto:

1) a heavy chain variable region including a CDR1 region represented by SEQ ID NO: 1, a CDR2 region represented by SEQ ID NO: 2 and a CDR3 region represented by SEQ ID NO: 3, and a light chain variable region including a CDR1 region represented by SEQ ID NO: 4, a CDR2 region represented by SEQ ID NO: 5 and a CDR3 region SEQ ID NO: 6;

2) a heavy chain variable region including a CDR1 region represented by SEQ ID NO: 7, a CDR2 region represented by SEQ ID NO: 8 and a CDR3 region represented by SEQ ID NO: 9, and a light chain variable region including a CDR1 region represented by SEQ ID NO: 10, a CDR2 region represented by SEQ ID NO: 11 and a CDR3 region represented by SEQ ID NO: 12;

3) a heavy chain variable region including a CDR1 region represented by SEQ ID NO: 13, a CDR2 region represented by SEQ ID NO: 14 and a CDR3 region represented by SEQ ID NO: 15, and a light chain variable region including a CDR1 region represented by SEQ ID NO: 16, a CDR2 region represented by SEQ ID NO: 17 and a CDR3 region represented by SEQ ID NO: 18; and 4) a heavy chain variable region including a CDR1 region represented by SEQ ID NO: 19, a CDR2 region represented by SEQ ID NO: 20 and a CDR3 region represented by SEQ ID NO: 21, and a light chain variable region including a CDR1 region represented by SEQ ID NO: 22, a CDR2 region represented by SEQ ID NO: 23 and a CDR3 region represented by SEQ ID NO: 24.

In one embodiment of the present invention, the antigen-binding fragment is preferably Fab, Fab', F(ab')2, scFv, Fv, dsFv, a diabody, Fd, Fd', a light chain or heavy chain including a CDR region of the present invention, or a variable domain including a CDR region of the present invention, but the present invention is not limited thereto.

In another embodiment of the present invention, the monoclonal antibody or an antigen-binding fragment thereof preferably includes one pair of a heavy chain variable region and a light chain variable region selected from the group consisting of a heavy chain variable region including a polypeptide sequence represented by SEQ ID NO: 25 and a light chain variable region including a polypeptide sequence represented by SEQ ID NO: 26; a heavy chain variable region including a polypeptide sequence represented by SEQ ID NO: 27 and a light chain variable region including polypeptide sequence represented by SEQ ID NO: 28; a heavy chain variable region including a polypeptide sequence represented by SEQ ID NO: 29 and a light chain variable region including a polypeptide sequence represented by SEQ ID NO: 30; and a heavy chain variable region including a polypeptide sequence represented by SEQ ID NO: 31 and a light chain variable region including a polypeptide sequence represented by SEQ ID NO: 32.

The antibody of the present invention or an antigen-binding fragment thereof also includes all mutants achieving the effects of the present invention, which are obtained through one or more mutations such as substitution, deletion, inversion or translocation of an antibody limited by the above-described sequence.

In addition, the present invention provides a polynucleotide encoding the monoclonal antibody or the antigen-binding fragment thereof.

The polynucleotide may be selected from the group consisting of SEQ ID NOs: 33 to 36, but the present invention is not limited thereto.

The present invention also provides an expression vector including the polynucleotide and a transformant into which the vector is introduced.

The expression vector including the polynucleotide encoding the monoclonal antibody according to the present invention may be, but is not particularly limited to, a vector capable of replicating and/or expressing the polynucleotide in eukaryotic or prokaryotic cells including mammalian cells (e.g., human, monkey, rabbit, rat, hamster, and mouse cells), plant cells, yeast cells or bacterial cells (e.g., *Escherichia coli*), and preferably, a vector that is operably linked to a suitable promoter such that the nucleotide can be expressed in host cells and includes at least one selection marker. As an example, the expression vector may be a form in which the polynucleotide is introduced into a phage, a plasmid, a cosmid, a mini-chromosome, a virus or a retrovirus vector.

The expression vector including a polynucleotide encoding the monoclonal antibody may be an expression vector which includes a polynucleotide encoding a heavy or light chain of the monoclonal antibody or an expression vector which includes both of polynucleotides encoding a heavy chain and a light chain.

A transformant into which the expression vector of the present invention is introduced may be, but is not particularly limited to, bacterial cells, such as *E. coli, Streptomyces* or *Salmonella typhimurium*; yeast cells; fungal cells such as *Pichia pastoris*; insect cells such as *Drozophila* or *Spodoptera* SD cells; animal cells such as Chinese hamster ovary (CHO) cells, SP2/0 (mouse myeloma), human lymphoblastoid, COS, NS© (mouse myeloma), 293T, Bowes melanoma cells, HT-1080, baby hamster kidney (BHK) cells, human embryonic kidney (HEK) cells or PERC.6 (human retinal cells); or plant cells, which are transformed by introducing the expression vector.

The term "introduction" used herein refers to a method of delivering the vector including a polynucleotide encoding the monoclonal antibody to host cells. The introduction may be performed by various methods known in the art, such as calcium phosphate-DNA coprecipitation, DEAF-dextran-mediated transfection, polybrene-mediated transfection, electroporation, microinjection, liposome fusion, Lipofectamine and protoplast fusion. In addition, transduction refers to the delivery of a desired material into cells using a viral particle through infection. Additionally, transduction may be introduction of a vector into host cells via gene bombardment. In the present invention, the introduction may be interchangeably used with transformation.

The present invention also provides a composition for diagnosing cancer, which includes the monoclonal antibody.

The term "cancer" used herein may be any cancer expressing CCSP-2, and examples include, but are not limited to, esophageal cancer, gastric cancer, colorectal cancer, rectal cancer, oral cancer, pharyngeal cancer, laryngeal cancer, lung cancer, colon cancer, breast cancer, cervical cancer, endometrial cancer, ovarian cancer, prostate cancer, testicular cancer, bladder cancer, kidney cancer, liver cancer, pancreatic cancer, bone cancer, connective tissue cancer, skin cancer, brain cancer, thyroid cancer, leukemia, Hodgkin's disease, soft tissue sarcoma, lymphoma and multiple myeloma hematologic cancer, and is preferably colorectal cancer or pancreatic cancer.

The term "diagnosis" used herein refers to confirmation of the presence, severity (symptoms) and/or characteristics of a pathological state. As used in the specification, the "diagnosis of colorectal cancer" is confirmation of the pathological state of colorectal cancer, for example, the onset of colorectal cancer, the progression of a colorectal cancer lesion, the location of colorectal cancer (colorectal cancer cells), or the stage of colorectal cancer. For more accurate diagnosis, it is important to accurately and rapidly distinguish colorectal cancer cells and/or tissue from normal cells or tissue.

As an exemplary embodiment of the present invention, the present invention provides a monoclonal antibody specifically binding to CCSP-2, thereby specifically detecting CCSP-2 at the protein level, and thus it is possible to accurately diagnose colorectal cancer and/or colorectal cancer cells and/or tissue. Particularly, colorectal tissue may be visualized using a labeling material for visualization, conjugated to the antibody, and thus can be effectively applied to endoscopic diagnosis of colorectal cancer.

The monoclonal antibody and cancer have been described above. A disease associated with the expression or the progression of the expression of CCSP-2 or a CCSP-2-mediated disease, for example, cancer may be diagnosed using a diagnostic composition including the CCSP-2-specific monoclonal antibody of the present invention.

The present invention also provides a kit for diagnosing cancer, which includes the composition for diagnosing cancer.

The composition and cancer have been described above. In addition, the kit for diagnosing cancer may be configured to further include a composition, solution or apparatus, which has one or more types of components suitable for an analysis method.

In the specification, by providing an antibody specifically binding to CCSP-2, which is a biomarker specifically expressed in colorectal cancer, a means useful for the measurement of CCSP-2 expression and/or a CCSP-2 expression level is provided, and therefore, this means may be effectively applied to the diagnosis of cancer, particularly, colorectal cancer. In addition, the antibody may be used in the visualization of cancer when used with various labeling materials, and applied in colorectal cancer endoscopy to provide more accurate information on the confirmation of the presence of colorectal cancer and lesions, and morphological observation of cancer sites, and may reduce a misdiagnosis rate related to colorectal cancer and contribute to early diagnosis. In addition, when a bioactive material such as a drug is bound to the antibody, the bioactive material may be specifically delivered to colorectal cancer, and therefore it may be used as a composition for the colorectal cancer-targeted delivery of the bioactive material.

The present invention provides a method of providing information for cancer diagnosis, which includes detecting a CCSP-2 protein in a biological sample isolated from a subject suspected of having cancer using the monoclonal antibody through an antigen-antibody reaction.

The monoclonal antibody, cancer, a subject and CCSP-2 protein have been described above. In the method of providing information for cancer diagnosis, the CCSP-2 protein may be detected by reacting a monoclonal antibody specific for CCSP-2 of the present invention with a biological sample isolated from a subject suspected of having cancer and detecting the formation of an antigen-antibody complex, thereby providing information for cancer diagnosis. Since the CCSP-2 is overexpressed in various cancer cells such as colorectal cancer or pancreatic cancer, cancer may be diagnosed by comparing the expression level with that of a control such as normal cells or tissue, but the present invention is not limited thereto.

The term "biological sample" used herein may refer to tissue, cells, whole blood, serum, plasma, a tissue autopsy sample (brain, skin, lymph node, spinal cord, etc.), cell culture supernatant, ruptured eukaryotic cells and a bacterial expression system, but the present invention is not limited thereto. These biological samples may be reacted with the antibody of the present invention with or without manipulation, thereby confirming the presence of a CCSP-2 protein or the presence or absence of cancer.

The term "antigen-antibody complex" used herein refers to a conjugate of a CCSP-2 protein antigen in a sample and the monoclonal antibody according to the present invention recognizing the same, and the formation of such an antigen-antibody complex may be detected by any method selected from the group consisting of a colorimetric method, an electrochemical method, a fluorometric method, luminometry, a particle counting method, visual assessment and a scintillation counting method. However, the method is not particularly limited thereto, and various applications may be used.

In the present invention, to detect the antigen-antibody complex, various markers may be used. As a specific example, the marker may be selected from the group consisting of an enzyme, a fluorescent material, a ligand, a luminescent material, a microparticle, and a radioactive isotope, but the present invention is not limited thereto.

Enzymes used as a detection marker include acetylcholinesterase, alkaline phosphatase, β-D-galactosidase, horseradish peroxidase, and β-lactamase, fluorescent materials used as a detection marker include fluorescein, $Eu^{3+}$, $Eu^{3+}$ chelate and cryptate, ligands used as a detection marker include a biotin derivative, luminescent materials used as a detection marker include acridinium ester and an isoluminol derivative, microparticles used as a detection marker include colloidal gold and colored latex, and radioactive isotopes used as a detection marker include 57Co, 3H, 125I, 125I-Banton and Hunter reagents.

Preferably, the antigen-antibody complex may be detected by ELISA. ELISA includes various ELISA method, for example, direct ELISA using a labeled antibody recognizing an antigen attached to a solid support, indirect ELISA using a labeled secondary antibody recognizing a capture antibody in an antibody complex recognizing an antigen attached to a solid support, direct sandwich ELISA using another labeled antibody recognizing an antigen in an antibody-antigen complex attached to a solid support, and indirect sandwich ELISA reacting with another antibody recognizing an antigen in an antibody-antigen complex attached to a solid support and using a labeled secondary antibody recognizing the antibody.

The monoclonal antibody may have a detection marker, and when there is no detection marker, these monoclonal antibodies may be captured and detected by treating another antibody having a detection marker.

In one embodiment of the present invention, by confirming that the anti-CCSP-2 antibody of the present invention specifically recognizes CCSP-2 using an antigen-antibody reaction, it was shown that the antibody of the present invention can be effectively used for diagnosis of various types of cancer such as colorectal cancer.

Hereinafter, the monoclonal antibody according to the present invention, or an antigen-binding fragment thereof will be described in detail with reference to ex pies.

EXAMPLES

Preparation Example. Construction of CCSP-2 Antigen

FIG. 1 is a schematic diagram illustrating the strategy of cloning a variable region of a scFv antibody according to one embodiment of the present invention.

Figure 2:
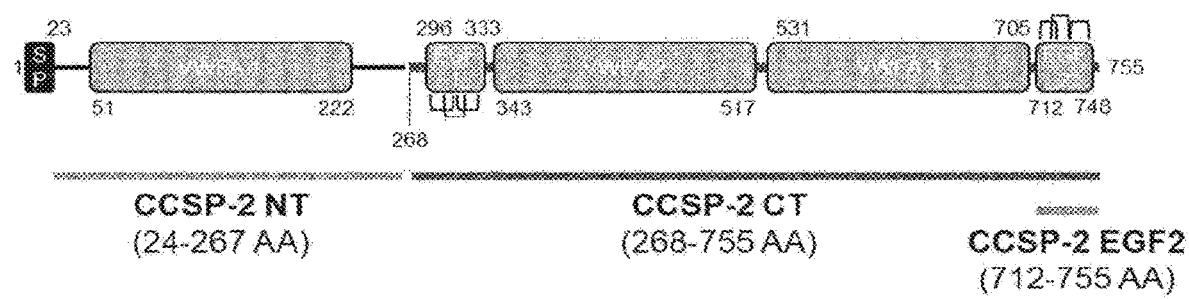
FIG. 2 is a schematic diagram illustrating antigen CCSP-2-NT, CCSP-2-CT and CCSP-2-EGF2 sites of CCSP-2.

In addition, FIG. 2 is a schematic diagram illustrating CCSP-2 antigens (NT, CT and EGF2) according to one embodiment of the present invention.

Among the antigens, CCSP-2-CT and CCSP-2-EGF2 contain the EGF2 domain.

Specifically, CCSP-2-CT (268 aa-755 aa of AY57297231) was inserted into a pBT7-C-his vector (Bioneer, Korea) to be transduced into Origami2 (DE3) (Novagen, MA, USA).

CCSP-2-EGF2 (712 aa-755 aa of AY572972.1) was inserted into a pBT7-N-His vector (Bioneer, Korea) to be transduced into Origami2 (DE3) (Novagen, MA, USA).

Figure 3:
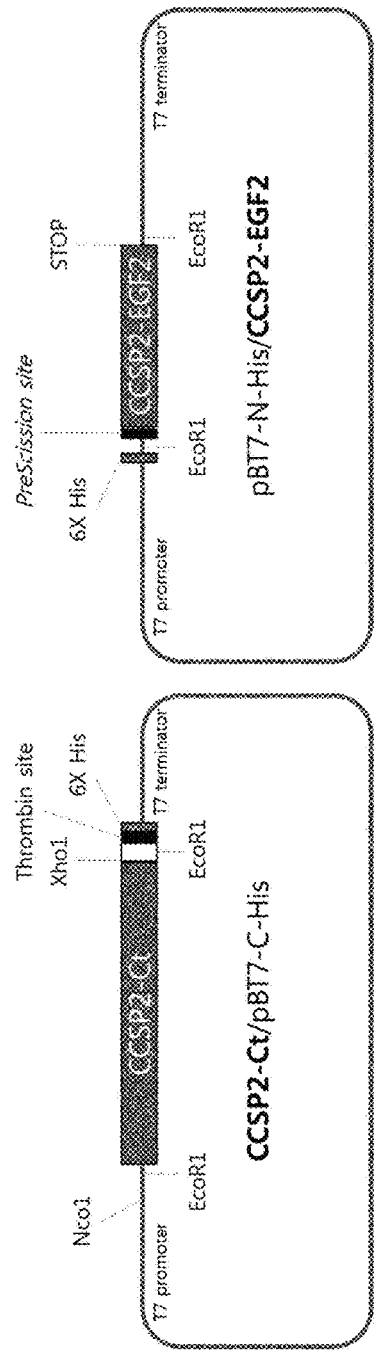
FIG. 3 is a schematic diagram illustrating respective expression vectors of CCSP-2-CT and CCSP-2-EGF2 antigens.

FIG. 3 is a schematic diagram illustrating respective expression vectors of CCSP-2-CT and CCSP-2-EGF2.

The CCSP-2-CT and the CCSP-2-EGF2 were purified with Ni-NTA agarose beads (Qiagen, USA).

Example 1. Preparation of Human-Derived Anti-EGF2 Antibody 1-1. Selection of Anti-EGF2 Antibody from Human Naive Antibody Library 1-1-1. Isolation of Human Mononuclear Cells Peripheral blood mononuclear cells were collected by treating 16 samples of human tonsil tissue with a Ficoll-Paque solution (GE Healthcare), and total RNA was extracted using a TRI reagent (Invitrogen). First strand cDNA was synthesized using oligo-dT primers and the Superscript® III First-Strand Synthesis System (Invitrogen).

1-1-2. Construction of Human scFv Library

A scFv library was constructed from cDNA obtained from the human mononuclear cells using primers in the following Table 1, specific for a heavy chain variable region and a light chain variable region of an immunoglobulin, and the Expand High Fidelity PCR system (Roche Molecular Systems).

TABLE 1

| Vκ Primers | |
|---|---|
| Forward | |
| HSCK1-F | GGGCCCAGGCGGCCGAGCTCCAGATGACCCAGTCTCC (SEQ ID NO: 37) |

TABLE 1-continued

| | |
|---|---|
| HSCK24-F | GGGCCCAGGCGGCCGAGCTCGTGATGACYCAGTCTCC (SEQ ID NO: 38) |
| HSCK3-F | GGGCCCAGGCGGCCGAGCTCGTGWTGACRCAGTCTCC (SEQ ID NO: 39) |
| HSCK5-F | GGGCCCAGGCGGCCGAGCTCACACTCACGCAGTCTCC (SEQ ID NO: 40) |

Reverse

| | |
|---|---|
| HSCJK14o-B | GGAAGATCTAGAGGAACCACCTTTGATYTCCACCTTGGTCCC (SEQ ID NO: 41) |
| HSCJK2o-B | GGAAGATCTAGAGGAACCACCTTTGATCTCCAGCTTGGTCCC (SEQ ID NO: 42) |
| HSCJK3o-B | GGAAGATCTAGAGGAACCACCTTTGATATCCACTTTGGTCCC (SEQ ID NO: 43) |
| HSCJK5o-B | GGAAGATCTAGAGGAACCACCTTTAATCTCCAGTCGTGTCCC (SEQ ID NO: 44) |

Vλ Primers

Forward

| | |
|---|---|
| HSCLam1a | GGGCCCAGGCGGCCGAGCTCGTGBTGACGCAGCCGCCCTC (SEQ ID NO: 45) |
| HSCLam1b | GGGCCCAGGCGGCCGAGCTCGTGCTGACTCAGCCACCCTC (SEQ ID NO: 46) |
| HSCLam2 | GGGCCCAGGCGGCCGAGCTCGCCCTGACTCAGCCTCCCTCCGT (SEQ ID NO: 47) |
| HSCLam3 | GGGCCCAGGCGGCCGAGCTCGAGCTGACTCAGCCACCCTCAGTGTC (SEQ ID NO: 48) |
| HSCLam4 | GGGCCCAGGCGGCCGAGCTCGTGCTGACTCAATCGCCCTC (SEQ ID NO: 49) |
| HSCLam6 | GGGCCCAGGCGGCCGAGCTCATGCTGACTCAGCCCCACTC (SEQ ID NO: 50) |
| HSCLam78 | GGGCCCAGGCGGCCGAGCTCGTGGTGACYCAGGAGCCMTC (SEQ ID NO: 51) |
| HSCLam9 | GGGCCCAGGCGGCCGAGCTCGTGCTGACTCAGCCACCTTC (SEQ ID NO: 52) |

Reverse

| | |
|---|---|
| HSCJLam1236 | GGAAGATCTAGAGGAACCACCGCCTAGGACGGTCASCTTGGTSCC (SEQ ID NO: 53) |
| HSCJLam57 | GGAAGATCTAGAGGAACCACCGCCGAGGACGGTCAGCTSGGTSCC (SEQ ID NO: 54) |

VH Primers

Forward

| | |
|---|---|
| HSCVH1-FL | GGTGGTTCCTCTAGATCTTCCTCCTCTGGTGGCGGTGGCTCGGGCGGTGG TGGGCAGGTGCAGCTGGTGCAGTCTGG (SEQ ID NO: 55) |
| HSCVH2-FL | GGTGGTTCCTCTAGATCTTCCTCCTCTGGTGGCGGTGGCTCGGGCGGTGG TGGGCAGATCACCTTGAAGGAGTCTGG (SEQ ID NO: 56) |
| HSCVH35-FL | GGTGGTTCCTCTAGATCTTCCTCCTCTGGTGGCGGTGGCTCGGGCGGTGG TGGGGAGGTGCAGCTGGTGSAGTCTGG (SEQ ID NO: 57) |
| HSCVH3a-FL | GGTGGTTCCTCTAGATCTTCCTCCTCTGGTGGCGGTGGCTCGGGCGGTGG TGGGGAGGTGCAGCTGKTGGAGTCTG (SEQ ID NO: 58) |

TABLE 1-continued

| | |
|---|---|
| HSCVH4-FL | GGTGGTTCCTCTAGATCTTCCTCCTCTGGTGGCGGTGGCTCGGGCGGTGG<br>TGGGCAGGTGCAGCTGCAGGAGTCGGG<br>(SEQ ID NO: 59) |
| HSCVH4a-FL | GGTGGTTCCTCTAGATCTTCCTCCTCTGGTGGCGGTGGCTCGGGCGGTGG<br>TGGGCAGGTGCAGCTACAGCAGTGGGG<br>(SEQ ID NO: 60) |
| Reverse | |
| HSCG1234-B | CCTGGCCGGCCTGGCCACTAGTGACCGATGGGCCCTTGGTGGARGC<br>(SEQ ID NO: 61) |
| HSCM-B | CCTGGCCGGCCTGGCCACTAGTAAGGGTTGGGGCGGATGCACTCCC<br>(SEQ ID NO: 62) |
| Overlap Extension Primers | |
| RSC-F | GAGGAGGAGGAGGAGGAGGCGGGGCCCAGGCGGCCGAGCTC<br>(SEQ ID NO: 63) |
| RSC-B | GAGGAGGAGGAGGAGGAGCCTGGCCGGCCTGGCCACTAGTG<br>(SEQ ID NO: 64) |

In each reaction, 2 µL of cDNA was mixed with 60 pmol of each primer, 10 µL of 10× reaction buffer, 8 µL of 2.5 mM dNTP (Promega), 0.5 µL of Tap DNA polymerase and water so that a final volume became 100 µL. PCR was performed under the following conditions: 30 cycles, 15 sec at 94° C., 30 sec at 56° C., 90 sec at 72° C., and 10 min at 72° C. (final extension). A fragment with a length of approximately 350 bp was loaded on a 1.5% agarose gel for electrophoresis, and purified using a QIAGEN II Gel Extraction Kit (QIAGEN). The purified PCR product was read at OD 260 nm and quantified (1 OD unit=50 µg/mL).

In second PCR, first VL and VH products were randomly linked by overlap extension PCR. Each PCR was performed with a mixture having a final concentration of 100 µL, which was prepared by mixing 100 ng of the purified VL and VH products, 60 pmol of each primer, 10 µL of 10× reaction buffer, 8 µL of 2.5 mM dNTP and 0.5 µL of Taq DNA polymerase with water. PCR was performed under the following conditions: 25 cycles, 15 sec at 94° C., 30 sec at 56° C., 2 min at 72° C., and 10 min at 72° C. (final extension). A scFv fragment having a length of approximately 700 bp was loaded on a 1.5% agarose gel for electrophoresis, and then purified using a QIAGEN II Gel Extraction Kit (QIAGEN). The purified PCR product was read at OD 260 nm and quantified (1 OD unit=50 µg/mL).

1-1-3. Library Ligation and Transformation

For cloning, a scFv fragment, which is the PCR product, and a pComb3X-SS vector (The Scripps Research Institute) were cleaved using a SfiI restriction enzyme.

Specifically, 10 µg of the purified overlap PCR product was mixed with 360 units of SifI (16 units per µg DNA, Roche Molecular Systems), 20 µL of 10× reaction buffer and water, and adjusted to have a final volume of 200 µL. 20 µg of the pComb3X-SS vector was mixed with 120 units of Sf (6 units per µg DNA), 20 µL of 10× reaction buffer and water, and adjusted to have a final volume of 200 µL. The mixture was cleaved for 8 hours at 50° C. A scFv fragment having a length of approximately 700 bp and a vector having a length of 3,400 bp were loaded on a 1% agarose gel for electrophoresis, and purified using a QIAGEN II Gel Extraction Kit (QIAGEN). 1,400 ng of the SfiI-cleaved pComb3X vector and 700 ng of a scFv fragment were mixed with 40 µL of 5× ligase buffer, 10 µL of T4 DNA ligase (Invitrogen) and water so that a final volume became 200 µL, and incubated at 16° C. for 16 hours, followed by ligation. Afterward, the ligated product was precipitated with ethanol, and only the DNA pellet was dissolved in 15 µL of water.

The ligated library sample was transformed into an E. coli strain, ER2738 (New England Biolabs, Inc.) through electroporation using a gene pulser (Bio-Rad Laboratories). The cells were mixed in 5 mL of a Super Broth (SB) medium at 37° C., and incubated while stirring for 1 hour at 250 rpm. Afterward, 10 mL of SB medium and 3 µL of 100 mg/mL carbenicillin were added to the culture medium. 0.1 µL, 1 µL or 10 µL of the culture was plated on a Luria Broth (LB) agar plate containing 50 µg/mL of carbenicillin to determine a library size. The cell culture was further stirred for 1 hour, and then stirred for one more hour after 4.5 µL of 100 mg/mL carbenicillin was added. 2 mL of VCM13 helper phage (>1,011 cfu/mL), 183 mL of pre-warmed SB and 92.5 µL of 100 mg/mL carbenicillin were added to the cell culture, and stirred at 250 rpm and 37° C. for 2 hours. 280 µL (50 mg/mL) of kanamycin was added to the cell culture, and stirred at 250 rpm and 37° C. overnight.

The next day, the cell culture was centrifuged at 3,000 g and 4° C. using a high-speed centrifuge (Beckman, JA-10 rotor). Afterward, a bacterial pellet was stored to prepare phagemid DNA, and a supernatant was transferred to a sterilized centrifuge tube. Subsequently, 8 g of polyethylene glycol-8000 (PEG-8000, Sigma) and 6 g of sodium chloride (NaCl, Merck) were added and stored on ice for 30 minutes, and the supernatant was centrifuged at 15,000 g and 4° C. for 15 minutes. The supernatant was discarded, and the phage pellet was resuspended in Tris-buffered saline (TBS) containing 1% BSA.

Example 1-2. Library Panning on Immobilized Antigen (Bio-Panning)

Bio-panning was performed using magnetic beads (Dynabeads M-270 Epoxy, Invitrogen). 3 µg of a C-terminus fragment EGF2 recombinant protein was agitated with 1×10⁷ beads at room temperature for 20 hours to coat an antigen. The coated beads were washed with PBS four times, blocked with 3% BSA-containing phosphate-buffered saline (PBS) at room temperature for 1 hour, and incubated with the phage-displayed scFv obtained in Example 3-3 at room temperature for 2 hours. To remove a phage not binding to the bead-coated antigen, after washing with 0.05% Tween20/PBS, the bound phage was eluted using 50 μL of 0.1M glycine/hydrogen chloride (0.1 M Glycine-HCl, pH 2.2), and neutralized with 3 μL of 2 M Tris-HCl (pH 9.1). *E. coli* ER2738 was transfected with the phage-containing supernatant, and rescued using a VCSM13 helper phage for overnight amplification of phages. In addition, a cell culture infected by the phage was plated on a LB agar plate containing 50 μg/mL of carbenicillin to determine input and output phage titers. The next day, PEG-8000 and NaCl were added to precipitate only phages, and the precipitated phages were used for the next round of bio-panning.

Panning was performed up to four times by repeating the above-described process. In addition, phages having high affinity were selected and enriched by gradually increasing the number of washings, for example, once in the first round and eventually three times in the fourth round.

Example 1-3. Selection of Clones by Phage ELISA

To analyze clones selected from bio-panning, ELISA was performed to confirm whether a randomly-selected phage-displayed scFv individual clone has binding ability to a CCSP-2-EGF2 recombinant protein (monomer).

The CCSP-2-EGF2 recombinant protein (monomer) was diluted in 0.1 M NaHCO$_3$ buffer, and coated on a 96-well microtiter plate at 100 ng/well at 4° C. for 16 hours, and the next day, blocked with 3% BSA/PBS at 37° C. for 1 hour. Subsequently, a phage supernatant was mixed with 6% BSA/PBS at an equal amount, and incubated at 37° C. for 2 hours. After washing with 0.05% Tween20/PBS, a HRP conjugated anti-M13 antibody (a-M13-HRP, Pierce Chemical Co.) was diluted at a ratio of 1/5000 and added at 50 μL each to the plate, followed by incubation for 1 hour at 37° C. After incubation, for a color reaction after washing, 1 μg/mL of 2,2'-azino-bis(3-ethylbenzothiazoline-6-sulphonic acid) (ABTS, Amresco) in 0.05 M citrate buffer and 0.1% H$_2$O$_2$ were added to each well, followed by color development. And then, absorbance was measured at 405 nm. The result is shown in FIGS. 4A and 4B.

Figure 4:
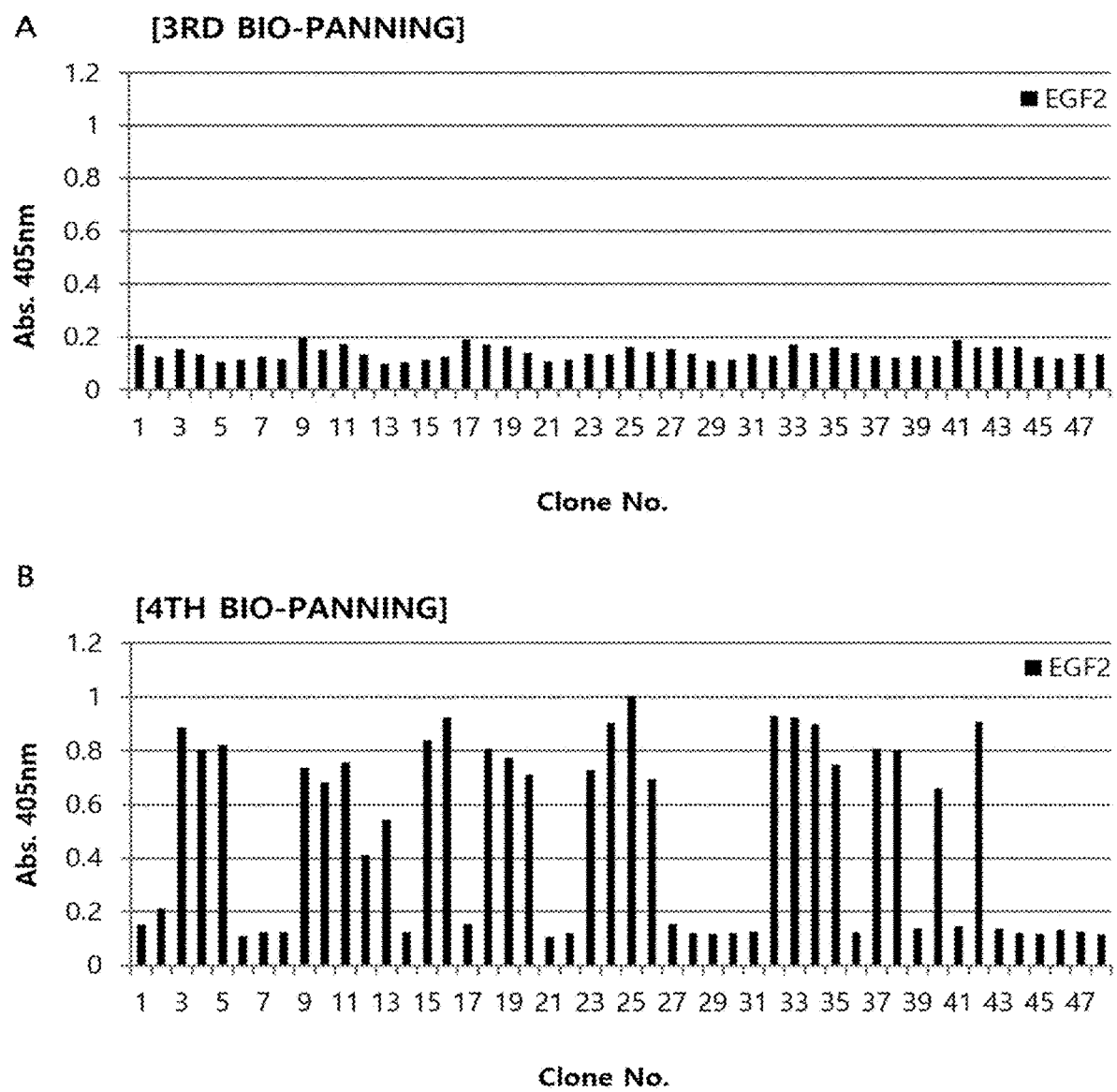
FIGS. 4A and 4B show phage ELISA results obtained by ELISA on 48 clones from produced phages (output) of third and fourth bio-panning, respectively.

FIGS. 4A and 4B show phage ELISA results obtained by ELISA on 48 clones from produced phages (output) of third and fourth bio-panning, respectively. A total of 11 types of scFv clones with different sequences were obtained by analyzing the genetic sequences of 24 clones with high absorbance among clones binding to the CCSP-2-EGF2 recombinant protein.

Example 1-4. Preparation of Anti-CCSP-2-EGF2 scFv hFc1 Fusion Protein 1-4-1. Anti-CCSP-2-EGF2 scFv Subcloning (scFvhFc1) into Mammalian Expression Vector Genes encoding IgG2 hinge and human IgG1 hybrid CH2-CH3 were inserted into a pCEP4 vector (Invitrogen) using restriction enzymes HindIII (New England Biolabs) and XhoI (New England Biolabs). A gene encoding anti-CCSP-2-EGF2 scFv was subcloned into the 5' end of the Fc region by two SfiI restriction sites. For a light chain, a human immunoglobulin Fc gene was subcloned into a mammalian expression vector. For a heavy chain, genes encoding a human CH1 region and a region from an IgG2 hinge to a human IgG1 hybrid CH2-CH3 region were subcloned into a mammalian expression vector (see FIG. 5).

Figure 5:
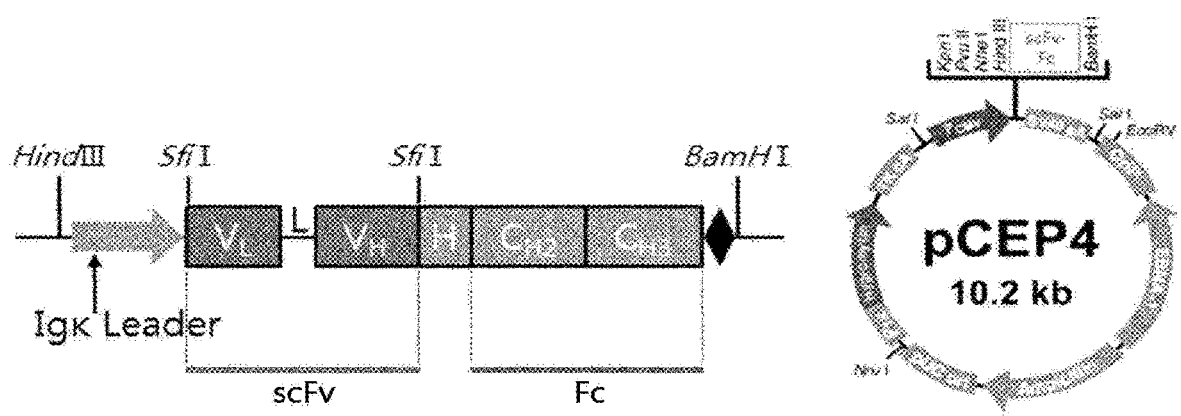
FIG. 5 is a genetic map of an expression vector according to one embodiment of the present invention.

FIG. 5 is a genetic map of an expression vector according to one embodiment of the present invention.

1-4-2. Transfection and Protein Purification

Transfection was performed on an overexpressed recombinant protein. 2 μg of a mammalian expression vector and 4 μg of polyethyleneimine (PEI, Polysciences, Warrington, PA, USA) per mL of a culture volume were mixed in 150 mM sodium chloride (NaCl, Merck) corresponding to 1/10 of the cell culture volume, and maintained at room temperature for 15 minutes. The mixture was added to mammalian cells, HEK293F (1×10$^6$ cells/mL, Invitrogen) used for a protein overexpression system, and cultured in a Freestyle™ 293 expression medium (Invitrogen) containing 100 U/mL penicillin and streptomycin (Invitrogen) for 6 days at 37° C. and 7% CO$_2$ while stirring at 135 rpm.

A supernatant of the cell culture was harvested, and to purify an Fc-fusion protein, an affinity gel chromatography method using protein A was used. After isolated scFv was purified through dialysis using PBS buffer, SDS-PAGE was performed to confirm a molecular weight of approximately 55 kDa (see FIG. 6).

Figure 6:
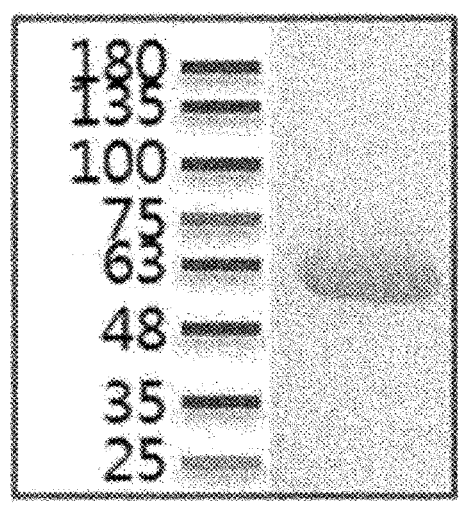
FIG. 6 is an SDS-PAGE gel image showing the molecular weight of HN-1 of scFv produced by the present invention.

FIG. 6 is an SDS-PAGE gel image showing the molecular weight of HN-1 of scFv produced by the present invention.

Example 1-5. Confirmation of Binding Ability of Recombinant Antibody 1-5-1. Western Blotting CCSP-2 protein was prepared per domain, denaturation buffer was added thereto, followed by heating for 10 minutes. Then, SDS-PAGE electrophoresis was performed by loading a denatured sample on a prepared gel. After electrophoresis, the gel was not stained, and for an immunological assay, the protein was transferred to Trans-Blot Turbo™ Mini PVDF Transfer Packs (Bio-Rad) through an electro-transfer method. To inhibit a non-specific reaction, the gel was immersed in a 5% skim milk/TBST solution and treated on a stirrer for 1 hour. As a primary antibody, scFv obtained in Example 1-4-2 was diluted to a predetermined concentration, and as a secondary antibody, a HRP-conjugated anti-human immunoglobulin Fc secondary antibody (Invitrogen) was used. Each antibody reaction was performed for 1 hour, and after each step, the reaction product was washed with a 0.1% Tween 20-containing TBST solution three times. Finally, to confirm an antigen-antibody reaction, an enhanced chemiluminescent (ECL) substrate was used (see FIG. 7).

Figure 7:
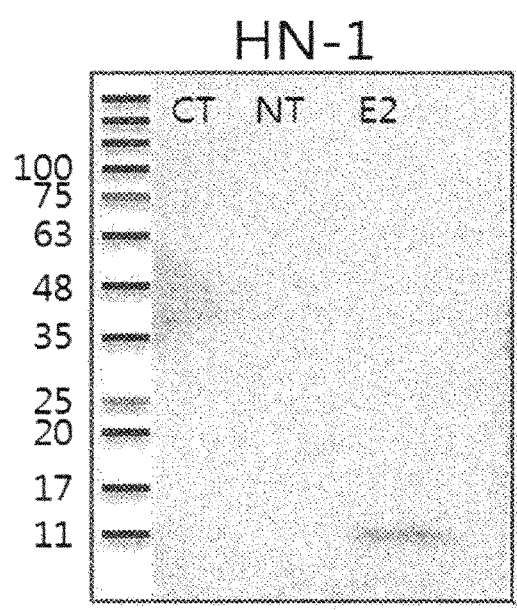
FIG. 7 shows a western blotting result for confirming the binding ability per antigen (CCSP-2) domain of HN-1 in scFv of the present invention.

FIG. 7 shows a western blotting result for confirming the binding ability per antigen (CCSP-2) domain of HN-1 in scFv of the present invention.

Referring to FIG. 7, it can be confirmed that the scFv antibody according to the present invention specifically binds to the EGF2 domain.

1-5-2. Sandwich ELISA

The scFv obtained according to Example 4-2 was coated on a 96-well plate at 10 μg/mL, followed by blocking with 5% skim milk/TBST for 1 hour. The antigen-immobilized wells were then washed with a 0.05% Tween 20-containing PBS buffer three times, the CCSP-2 protein was dispensed at 900 ng/mL, 300 ng/mL, 100 ng/mL, 33.3 ng/mL or 11.1 ng/mL to induce an antigen-antibody reaction for 1 hour. To measure the amount of antibodies reacting with the antigen, a reaction was performed for 1 hour by sequentially using an anti-CCSP-2 primary antibody (Cloud-Clone Corp., TX, USA) diluted at a ratio of 1:500 and a HRP-conjugated anti-rabbit IgG secondary antibody (Cell Signaling) diluted at a ratio of 1:2000. Afterward, color development was induced at room temperature for 20 minutes by dispensing a tetramethyl benzidine (TMB) substrate into the wells, and absorbance was then measured at 450 nm using a microplate reader (see FIG. 8).

Figure 8:
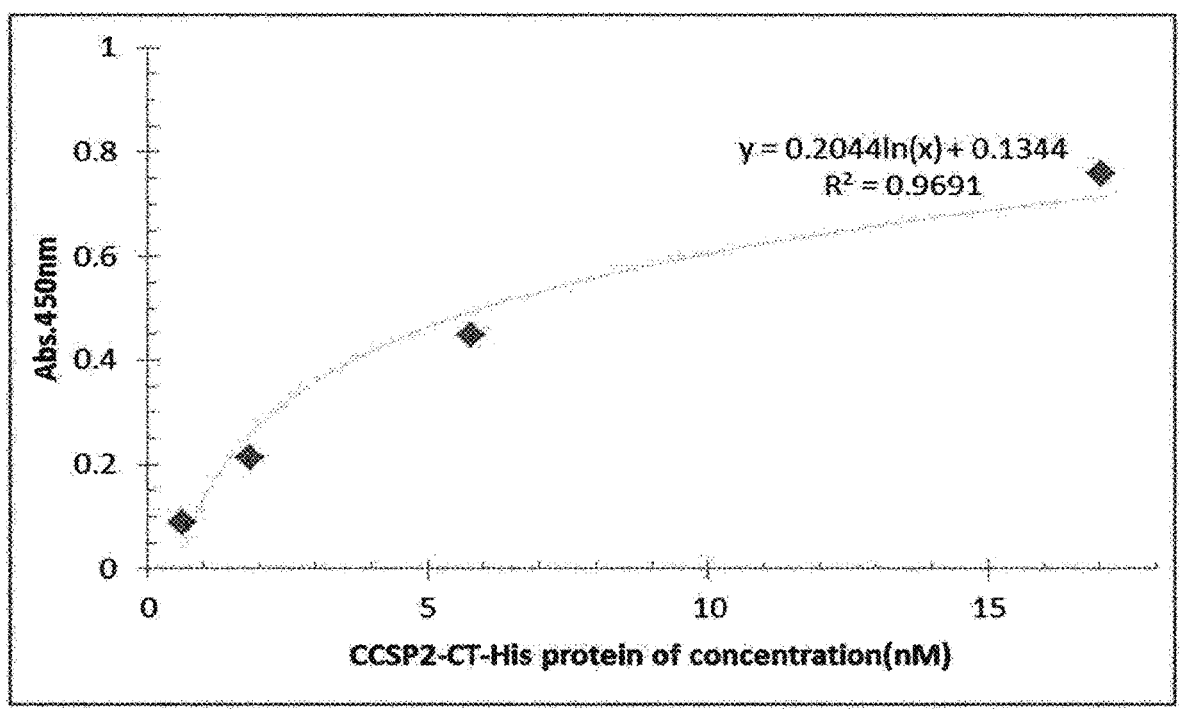
FIG. 8 is a graph showing an ELISA result obtained by analyzing the antigen (CCSP-2) binding ability of HN-1 in scFv of the present invention.

FIG. 8 is a graph showing an ELISA result obtained by analyzing the antigen (CCSP-2) binding ability of HN-1 in scFv of the present invention.

Referring to FIG. 8, it can be confirmed that the scFv antibody according to the present invention exhibited dose-dependent reactivity for the CCSP-2 protein.

As described above, the scFv antibody constructed by the present invention has a size of approximately 55 kDa, and a function as an antibody with binding ability to an antigen.

Example 1-6. Antibody Library Sequencing

For sequencing of a variable region of a selected antibody library, a random transformant was cultured to obtain a plasmid, followed by sequencing. The result is shown in Table 2 below. The sequences of the complementarity-determining site and skeletal part of VL-VH were confirmed by referencing the Chothia numbering scheme at ab Ysis (worldwide web.abysis.org/).

TABLE 2

| Clone | VL | | | VH | | |
|---|---|---|---|---|---|---|
| | CDR1 | CDR2 | CDR3 | CDR1 | CDR2 | CDR3 |
| HN-1 | SGSSRWY SEQ ID NO: 4 | SNDKRPS SEQ ID NO: 5 | GSGDSS SNPGI SEQ ID NO: 6 | GFTFSDR SEQ ID NO: 1 | SNAGGY SEQ ID NO: 2 | GASY DAIDA SEQ ID NO: 3 | water-in-oil emulsion containing MPL (monophosphorylate lipid A species), which is a toxin-free endotoxin, TDW and CWS, which are cell wall components of mycobacteria, in 2% squalene, and then subcutaneously injected into three chickens. The resulting antigen mixture was additionally injected by the same method three weeks later and then two weeks thereafter, resulting in immunization being performed a total of three times. The titer of immunized chicken antibody was determined by enzyme-linked immunosorbent assay (ELISA) using a HRP-conjugated anti-chicken IgG (Y) monoclonal antibody (rabbit anti-chicken IgG(Y)-HRP, Millipore Corporation, Billeria, MA, USA) as a secondary antibody.

2-1-2. Construction of Chicken scFv Library

Total RNA was extracted with a TRI reagent (Invitrogen, Carlsbad, CA, USA) from the spleen, bursa and bone marrow of the immunized chicken prepared in Example 2-1-1. First strand cDNA was synthesized using oligo-dT primers and Superscript™ III First-Strand Synthesis System (Invitrogen).

A scFv library for cDNA obtained from the immune system of a chicken was constructed using primers in Table 3 below, specific for a heavy chain variable region and a light chain variable region of an immunoglobulin, using an Expand High Fidelity PCR system (Roche Molecular Systems, IN, USA).

TABLE 3

| Vλ Primers | |
|---|---|
| CSCVK | GTG GCC CAG GCG GCC CTG ACT CAG CCG TCC TCG GTG TC (SEQ ID NO: 65) |
| CKJo-B | GGA AGA TCT AGA GGA CTG ACC TAG GAC GGT CAG G (SEQ ID NO: 66) |
| VH Primers | |
| CSCVHo-FL | GGT CAG TCC TCT AGA TCT TCC GGC GGT GGT GGC AGC TCC GGT GGT GGC GGT TCC GCC GTG ACG TTG GAC GCG (SEQ ID NO: 67) |
| CSCG-B | CTG GCC GGC CTG GCC ACT AGT GGA GGA GAC GAT GAC TTC GGT CC (SEQ ID NO: 68) |
| Overlap Extension Primers | |
| CSC-F | GAG GAG GAG GAG GAG GAG GTG GCC CAG GCG GCC CTG ACT CAG (SEQ ID NO: 69) |
| CSC-BGG | GAG GAG GAG GAG GAG GAG GAG CTG GCC GGC CTG GCC ACT AGT GGA (SEQ ID NO: 70) |

Example 2. Preparation of Chicken-Derived Anti-EGF2 Antibody

Example 2-1. Selection of Anti-EGF2 Antibody from Immune Antibody Library 2-1-1. Immunization 30 μg of the CCSP-2-EGF2 protein prepared in Example 1, as an antigen, was emulsified in a RIBI+MPL+TDM+CWS adjuvant (Sigma, St. Louis, Mo, USA), which is a In each reaction, 2 μL of cDNA was mixed with 60 pmol each of primers, 10 μL of 10× reaction buffer, 8 μL of 2.5 mM dNTP (Promega, Madison, WI, USA), 0.5 μL of Tap DNA polymerase and water so that a final volume became 100 μL. PCR was performed under the following conditions: 30 cycles, 15 sec at 94° C., 30 sec at 56° C. and 90 sec at 72° C., followed by final extension for 10 min at 72° C. A fragment with a length of approximately 350 bp was loaded on a 1.5% agarose gel for electrophoresis, and then purified using a QIAGEN II Gel Extraction Kit (QIAGEN, Valencia, CA, USA). The purified PCR product was read at OD 260 nm for quantification (1 OD unit=50 μg/mL).

In second PCR, the first VL and VH products were randomly linked by overlap extension PCR. Each PCR was performed with a mixture having a final volume of 100 μL prepared by mixing 100 ng of the purified VL and VH products, 60 pmol of each primer, 10 μL of 10× reaction buffer, 8 μL of 2.5 mM dNTP and 0.5 μL of Taq DNA polymerase with water. PCR was performed under the following conditions: 25 cycles, 15 sec at 94° C., 30 sec at 56° C., and 2 min at 72° C., followed by final extension for 10 min at 72° C. A scFv fragment with a length of approximately 700 bp was loaded on a 1.5% agarose gel for electrophoresis, and then purified using a QIAGEN H Gel Extraction Kit (QIAGEN). The purified PCR product was read at OD 260 nm for quantification (1 OD unit=50 μg/mL).

2-1-3. Ligation of Immune Antibody Library and Transformation

For cloning, a PCR product, that is, a scFv fragment, and a pComb3X-SS vector (The Scripps Research Institute, CA, USA) were cleaved with a SfiI restriction enzyme. 10 μg of the purified overlap PCR product was mixed with 360 units of SfiI (16 units per μg DNA, Roche Molecular Systems, Pleasanton, CA, USA), 20 μL of 10× reaction buffer and water so that a final volume became 200 μL. 20 μg of a pComb3X-SS vector was mixed with 120 units of SfiI (6 units per μg DNA), 20 μL of 10× reaction buffer and water, and adjusted to have a final volume to be 200 μL. The mixture was digested for 5 hours at 50° C. A scFv fragment with a length of approximately 700 bp and a vector with a length of 3,400 bp were loaded on a 1% agarose gel for electrophoresis, and purified using a QIAGEN II Gel Extraction Kit (QIAGEN, Valencia, CA, USA). 1,400 ng of SfiI-cleaved pComb3X vector and 700 ng of the scFv fragment were mixed with 40 μL of 5× ligase buffer, 10 μL of T4 DNA ligase (Invitrogen, Carlsbad, CA, USA) and water so that a final volume became 200 μL, and incubated at 16° C. for 16 hours for ligation. Afterward, the resulting product was precipitated with ethanol, thereby obtaining a DNA pellet, and then the pellet was dissolved in 15 μL of water.

The ligated library sample was transformed into an *E. coli* strain, ER2738 (New England Biolabs Inc, Hitchin, Hertfordshine, SG4 OTY, England, UK) through electroporation using a gene pulser (Bio-Rad Laboratories, Hercules, CA, USA). The cells were mixed at 37° C. in a 5 ml Super Broth (SB) medium, and incubated while stirring for 1 hour at 250 rpm. Subsequently, 10 mL SB medium and 3 μL of 100 mg/mL carbenicillin were added to the cell culture. 0.1 μL, 1 μL or 10 μL of the cell culture was plated on a Luria Broth (LB) agar plate containing 50 μg/mL of carbenicillin to determine a library size. The cell culture was further stirred for 1 hour, and then stirred for one more hour by adding 4.5 μL of 100 mg/mL carbenicillin thereto. 2 mL of VCM13 helper phage (>1,011 cfu/mL), 183 mL of pre-warmed SB and 92.5 μL of 100 mg/mL carbenicillin were added to the resulting cell culture, and then stirred at 250 rpm and 37° C. for 2 hours. 280 μL (50 mg/mL) of kanamycin was added to the resulting cell culture, and stirred at 250 rpm and 37° C. overnight.

The next day, the cell culture was centrifuged at 3,000 g and 4° C. using a high-speed centrifuge (Beckman, JA-10 rotor). Subsequently, a bacterial pellet was stored for preparation of phagemid DNA, and a supernatant was transferred to a sterilized centrifuge tube. Afterward, 8 g of PEG-8000 (Sigma) and 6 g of sodium chloride (NaCl, Merck) were added and stored on ice for 30 minutes, and a supernatant was centrifuged at 15,000 g and 4° C. for 15 minutes. The supernatant was discarded, and the phage pellet was resuspended in 1% BSA-containing TBS.

Example 2-2. Library Panning on Immobilized Antigen (Bio-Panning)

Bio-panning was performed using magnetic beads (Dynabeads M-270 Epoxy, Invitrogen). An antigen was coated by stirring 3 μg of CCSP-2-EGF2 recombinant protein with $1 \times 10^7$ beads at room temperature for 20 hours. The coated beads were washed with PBS four times, and the reaction was blocked with 3% BSA-containing PBS at room temperature for 1 hour, followed by incubation with the phage-displayed scFv obtained in Example 2-3 at room temperature for 2 hours. To remove a phage not binding to the antigen coated on the bead, the beads were washed with 0.05% Tween20/PBS, the bound phage was eluted with 50 μL of 0.1 M glycine-HCl (pH 2.2), and neutralized with 3 μL of 2 M Tris-HCl (pH 9.1). *E. coli* (ER2738) was transfected using the phage-containing supernatant, and rescued using a VCSM13 helper phage for overnight amplification of the phages. In addition, the cell culture transfected by the phages were plated on a LB agar plate containing 50 μg/mL of carbenicillin to determine the titers of input and output phages. The next day, only phages were precipitated by adding PEG-8000 and NaCl as described in Example 2-3, and the precipitated phages were used for the next round of bio-panning.

The panning was performed four times by repeating the above-described processes. In addition, washing was performed once in the first round, and phages with high affinity were selected and enriched by gradually increasing the number of washings, for example, one in the first round, and eventually four times in the fourth round.

Example 2-3. Selection of Clones by Phage ELISA

To analyze clones selected from the bio-panning, ELISA was performed to confirm whether a randomly-selected phage-displayed scFv individual clone has a binding ability to a recombinant protein (monomer) at the end of the EGF2-containing CCSP2-C.

Figure 9:
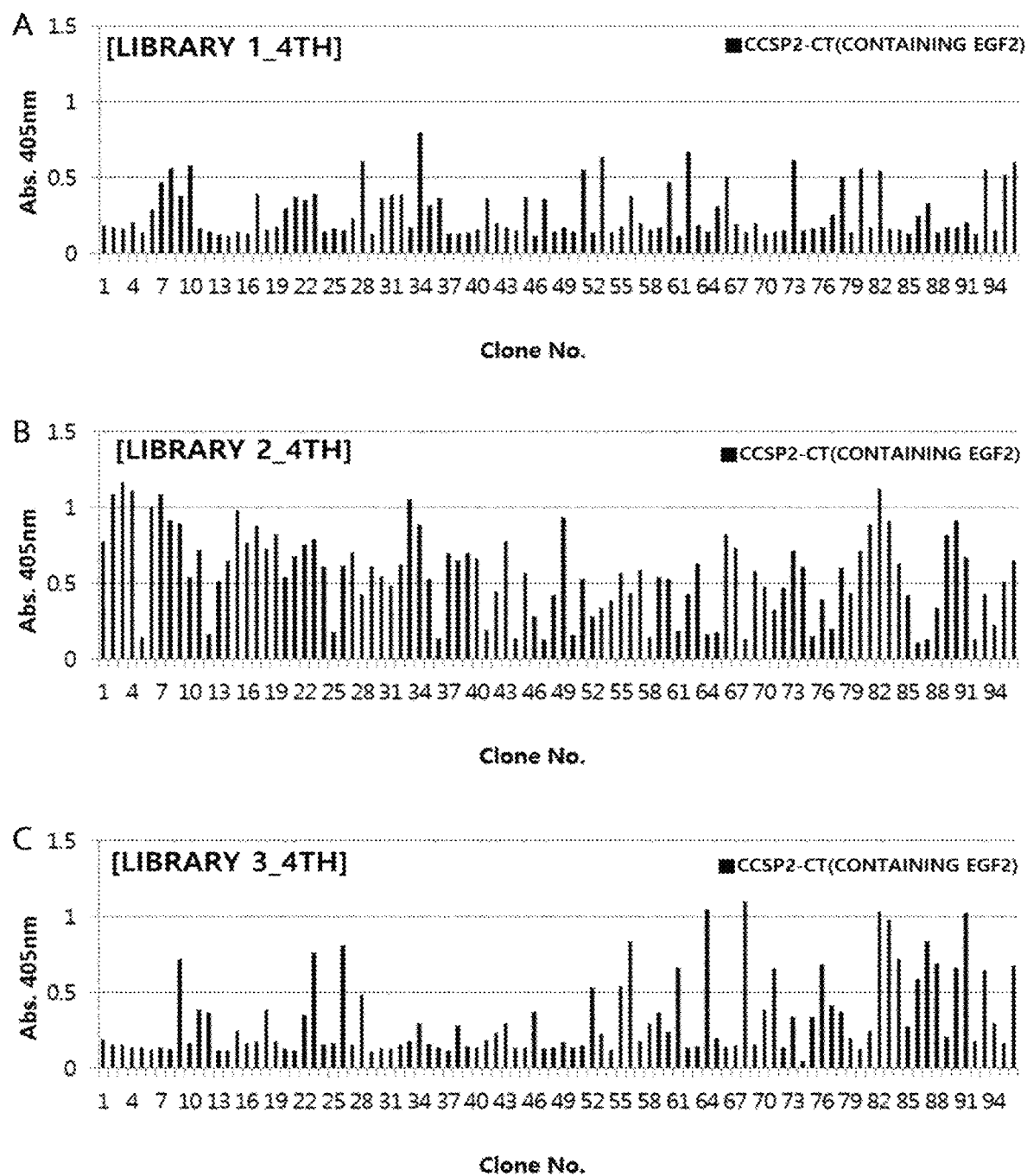
FIGS. 9A, 9B and 9C show antigen (CCSP-2)-binding phage ELISA results on 96 clones from the produced phages (output) of the fourth bio-panning of chicken libraries 1, 2 and 3.

The recombinant protein (monomer) at the end of the EGF2-containing CCSP2-C was diluted in 0.1 M $NaHCO_3$ buffer and applied to coat a 96-well microtiter plate at 100 ng/well and 4° C. for 16 hours, and the next day, the reaction was blocked with 3% BSA/PBS at 37° C. for 1 hour. Afterward, a phage supernatant was mixed with 6% BSA/PBS at the same amount, and incubated at 37° C. for 2 hours. The resulting product was washed with 0.05% Tween20/PBS, and a HRP conjugated anti-M13 antibody (a-M13-HRP, Pierce Chemical Co, Rockford, IL, USA) diluted at a ratio of 1/5000 was added at 50 μL each to the plate, followed by incubation for 1 hour at 37° C. After incubation, washing was performed, 1 μg/mL of 2,2'-azino-bis(3-ethylbenzothiazoline-6-sulphonic acid) (ABTS, Amresco, Solon, OH, USA) and 0.1% $H_2O_2$ in a 0.05 M citrate buffer solution were added to each well for color development, and color development was performed, followed by measurement of absorbance at 405 nm. FIGS. 9A, 9B and 9C show the results of analyzing 96 clones from the produced phages (output) by bio-panning of each chicken library 1, 2 or 3. The genetic sequences of 58 clones with high absorbance among clones simultaneously binding to the recombinant protein at the end of EGF2-containing CCSP2-C were analyzed, thereby obtaining a total of 8 types of scFv clones having different sequences.

Example 2-4. Preparation of Anti-CCSP-2-EGF2 scFv hFc1 Fusion Protein 2-4-1. Anti-CCSP-2-EGF2 scFv Subcloning (scFvhFc1) into Mammalian Expression Vector Genes encoding an IgG2 hinge and human IgG1 hybrid CH2-CH3 were inserted into a pCEP4 vector (Invitrogen) by HindIII (New England Biolabs) and XhoI (New England Biolabs) restriction enzymes. A gene encoding anti-CCSP-2-EGF2 scFv was subcloned into the 5' end of the Fc region by two SfiI restriction sites. For a light chain, a human immunoglobulin Fc gene was subcloned into a mammalian expression vector. For a heavy chain, genes encoding a human CH1 region and a region from an IgG2 hinge to a human IgG1 hybrid CH2-CH3 region were subcloned into a mammalian expression vector (see FIG. 10).

Figure 10:
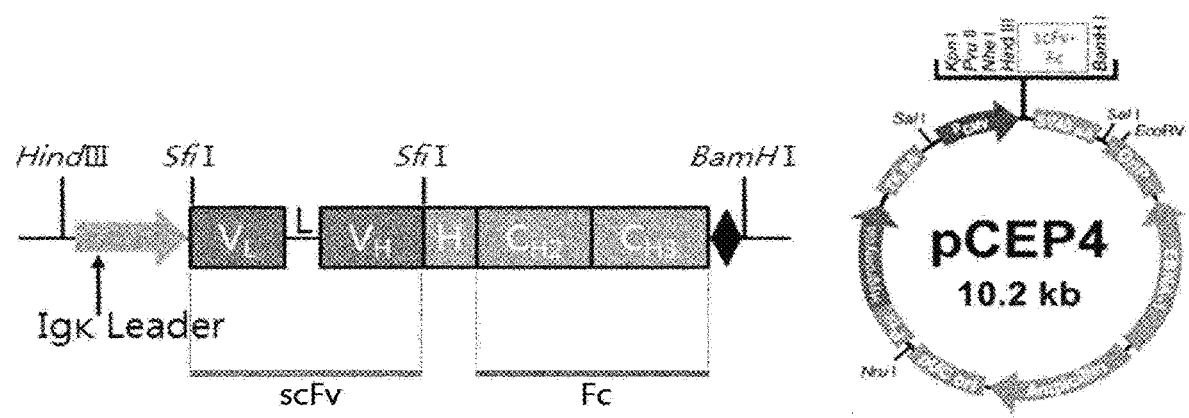
FIG. 10 is a genetic map representing an expression vector according to one embodiment of the present invention.

FIG. 10 is a genetic map of an expression vector according to one embodiment of the present invention.

2-4-2. Transfection and Protein Purification

Transfection was performed on an overexpressed recombinant protein. 2 μg of a mammalian expression vector and 4 μg of PEI (Polysciences, Warrington, PA, USA) per mL of a culture volume were mixed in 150 mM sodium chloride (NaCl, Merck) corresponding to 1/10 of the cell culture volume, and maintained at room temperature for 15 minutes. The mixture was added to mammalian cells, HEK293F ($1\times10^6$ cells/mL, Invitrogen) used for a protein overexpression system, and cultured in a Freestyle™ 293 expression medium (Invitrogen) containing 100 U/mL penicillin and streptomycin (Invitrogen) for 6 days at 37° C. and 7% $CO_2$ while stirring at 135 rpm.

A supernatant of the cell culture was harvested, and to purify an Fc-fusion protein, affinity gel chromatography using protein A was used. After isolated scFv was purified through dialysis using PBS buffer, SDS-PAGE was performed to confirm a molecular weight of approximately 55 kDa.

Example 2-5. Confirmation of Binding Ability of Recombinant Antibody 2-5-1. Western Blotting CCSP-2 protein was prepared per domain, denaturation buffer was added thereto, followed by heating for 10 minutes. Then, SDS-PAGE electrophoresis was performed by loading the denatured sample on a prepared gel. After electrophoresis, the gel was not stained, and for an immunological assay, the protein was transferred to Trans-Blot Turbo™ Mini PVDF Transfer Packs (Bio-Rad) by an electro-transfer method. To inhibit a non-specific reaction, the gel was immersed in a 5% skim milk/TBST solution and treated on a stirrer for 1 hour. As a primary antibody, the scFv obtained according to Example 4-2 diluted to a pre-determined concentration was used, and as a secondary antibody, a HRP-binding anti-human immunoglobulin Fc secondary antibody (Invitrogen) was used. Each antibody reaction was performed for 1 hour, and after each step, washing was performed three times with 0.05% Tween 20-containing PBS buffer. Finally, to confirm an antigen-antibody reaction, an enhanced chemiluminescent (ECL) substrate was used (see FIG. 11).

Figure 11:
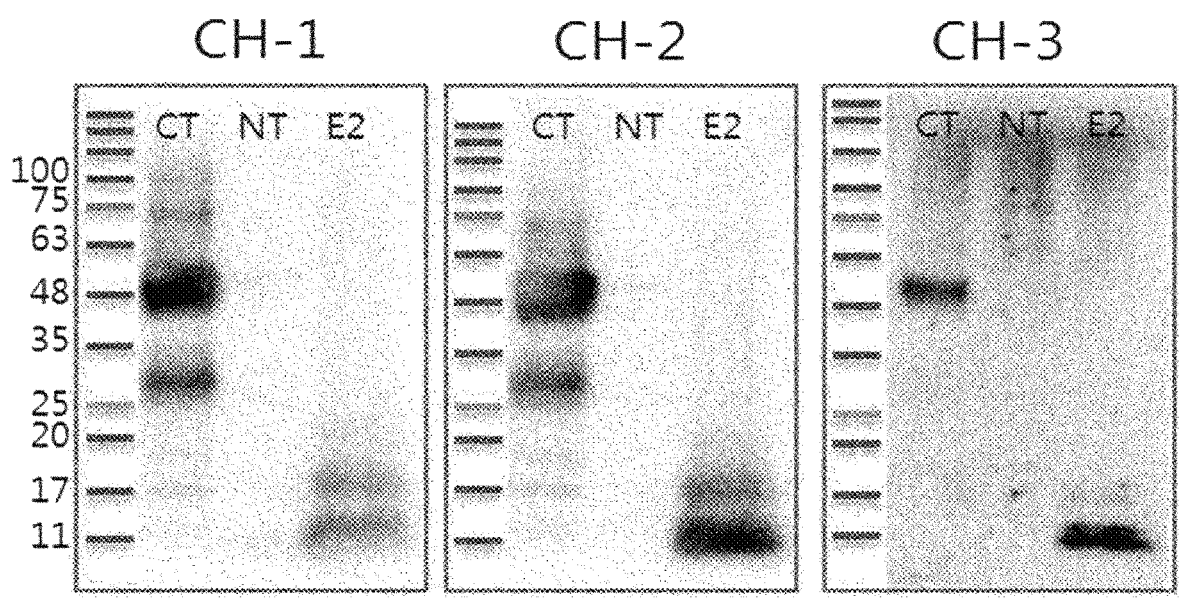
FIG. 11 shows western blotting results for confirming the binding ability per antigen (CCSP-2) domain of CH-1, CH-2 and CH-3 in scFv produced by the present invention.

FIG. 11 is a western blotting result for confirming the binding ability per antigen (CCSP-2) domain of CH-1, CH-2 and CH-3 in scFv produced according to the present invention.

2-5-2. Sandwich ELISA

A 96-well plate was coated with the scFv obtained according to Example 4-2 at a concentration of 10 μg/mL, and blocking was performed with 5% skim milk/TBST for 1 hour. The antigen-immobilized wells were then washed with 0.05% Tween 20-containing PBS buffer three times, and CCSP-2 protein was dispensed at 900 ng/mL 300 ng/mL, 100 ng/mL, 33.3 ng/mL or 11.1 ng/mL to induce an antigen-antibody reaction for 1 hour. To measure an amount of the antibodies reacting with the antigen, a reaction was performed for 1 hour sequentially using an anti-CCSP-2 (Cloud-Clone Corp., TX, USA) primary antibody diluted at a ratio of 1:500 and a HRP conjugated anti-Rabbit IgG secondary antibody (Cell Signaling) diluted at a ratio of 1:2000. Afterward, a tetramethylbenzidine (TMB) substrate was dispensed into the wells to induce color development at room temperature for 20 minutes, and then absorbance was measured at 450 nm using a microplate reader (see FIG. 12).

Figure 12:
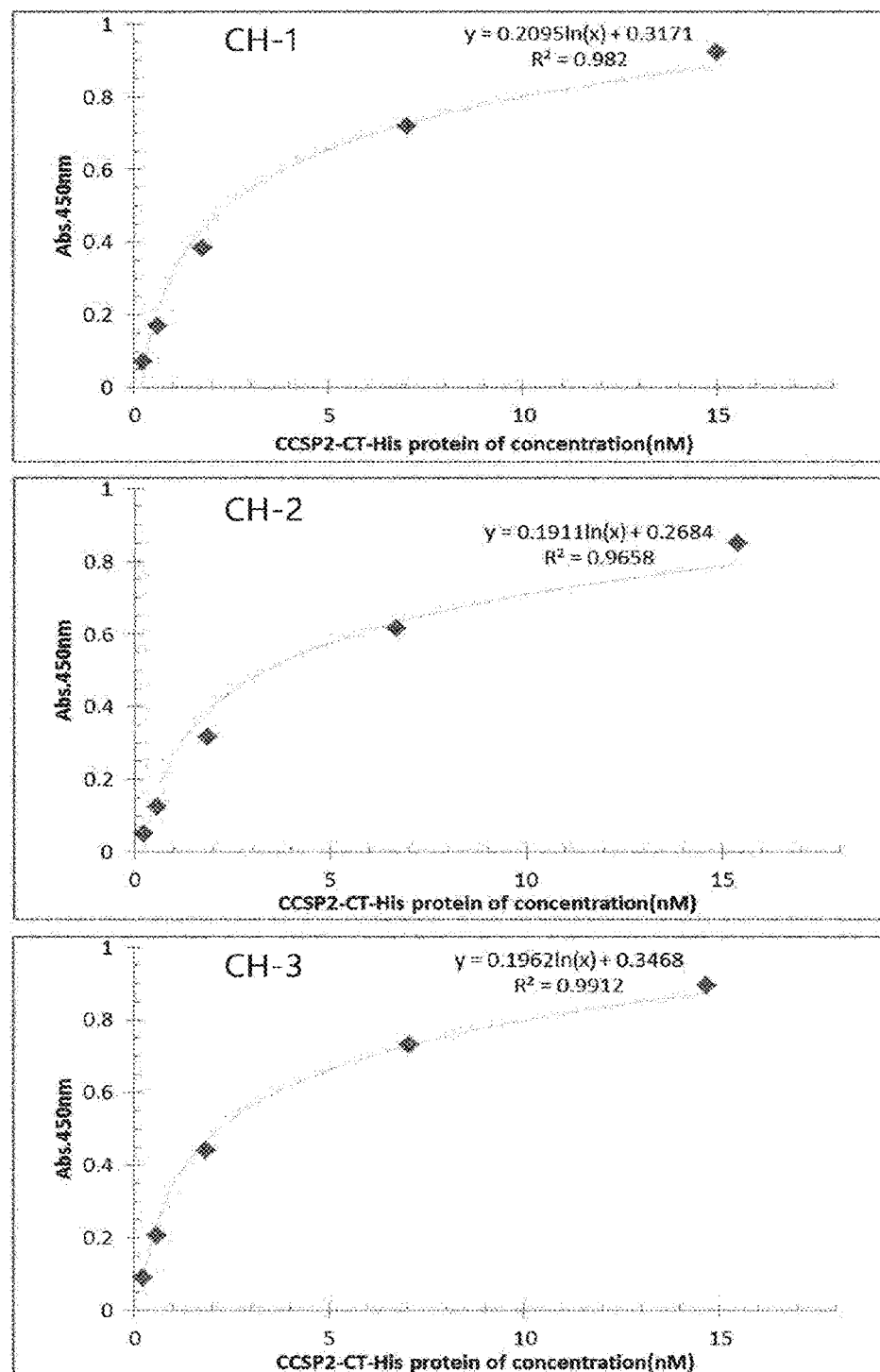
FIG. 12 is a set of graphs showing the ELISA results obtained by analyzing the antigen (CCSP-2) binding ability of CH-1, CH-2 and CH-3 in scFv of the present invention.

FIG. 12 is a set of graphs showing the ELISA results obtained by analyzing the antigen (CCSP-2) binding ability of CH-1, CH-2 and CH-3 in scFv of the present invention.

Referring to FIG. 12, it can be confirmed that the scFv antibody according to the present invention exhibits dose-dependent reactivity for the CCSP-2 protein.

As described above, the scFv antibody constructed according to the present invention has a size of approximately 55 kDa, and has a function as an antibody having binding ability to an antigen.

Example 2-6. Antibody Library Sequencing

For sequencing of a variable region in a selected antibody library, a random transformant was cultured to obtain a plasmid, and then sequencing was performed. The result is shown in Table 4 below. The sequences of the complementarity-determining site and skeletal part of VL-VH were confirmed by referencing the Chothia numbering scheme at abYsis (worldwide web.abysis.org/).

TABLE 4

| Clone | VL | | | VH | | |
|---|---|---|---|---|---|---|
| | CDR1 | CDR2 | CDR3 | CDR1 | CDR2 | CDR3 |
| 1 | SGGSNSYYG (SEQ ID NO: 10) | DNTNRPS (SEQ ID NO: 11) | GSTDSSYVDI (SEQ ID NO: 12) | GFSFSGV (SEQ ID NO: 7) | SSTGSG (SEQ ID NO: 8) | DAYGYRISGSWSYGYSIDA (SEQ ID NO: 9) |
| 2 | SGGGSYYG (SEQ ID NO: 16) | DNTNRPS (SEQ ID NO: 17) | GSADSSAEPV (SEQ ID NO: 18) | GFTFSSV (SEQ ID NO: 13) | SNTGSG (SEQ ID NO: 14) | DAYGYTTSGSWSYGYSIDA (SEQ ID NO: 15) |

TABLE 4-continued

| | VL | | | VH | | |
|---|---|---|---|---|---|---|
| Clone | CDR1 | CDR2 | CDR3 | CDR1 | CDR2 | CDR3 |
| 3 | SGDNSWYG (SEQ ID NO: 22) | DSDQRPS (SEQ ID NO: 23) | CGSYDSSAGYIGI (SEQ ID NO: 24) | GFSFSDR (SEQ ID NO: 19) | RSDGSS (SEQ ID NO: 20) | DYGNGGWIAGDIDA (SEQ ID NO: 21) |

Experimental Example 1. Effect Caused by Specific Binding to EGF2 Domain of CCSP-2

The antibodies according to the present invention were compared with the conventional antibodies against CCSP-2 to examine the effect caused by specific binding to the EGF2 domain of CCSP-2.

First, the recognition site of each CCSP2 antibody per domain was intended to be confirmed.

A recombinant protein of each domain EGF1, VWFA2, VWFA3 or EGF2 of CCSP-2-CT or CCSP-2 was prepared. In addition, taking advantage of the affinity of His-tag and the Ni-NTA resin, the recombinant proteins were purified. The purified recombinant proteins were loaded on a 12% SDS-PAGE gel at 100 ng/well, and CCSP-2 and domains of the CCSP-2 were detected with various CCSP-2 antibodies. The CCSP-2 antibodies used in the experiment were ① an antibody provided by Case Western Reserve University (not commercially available; hereinafter, CWRU antibody), ② Proteintech antibody, and ③ Cloud-Clone antibody.

FIG. 13A is a schematic diagram illustrating the locations of CCSP2 antibody per domain, and which domain is recognized by each CCSP-2 antibody.

FIG. 13B is western blotting results showing that the CWRU antibody specifically recognizes the EGF2 domain, and the Proteintech antibody specifically recognizes the VWFA2 domain.

Figure 13:
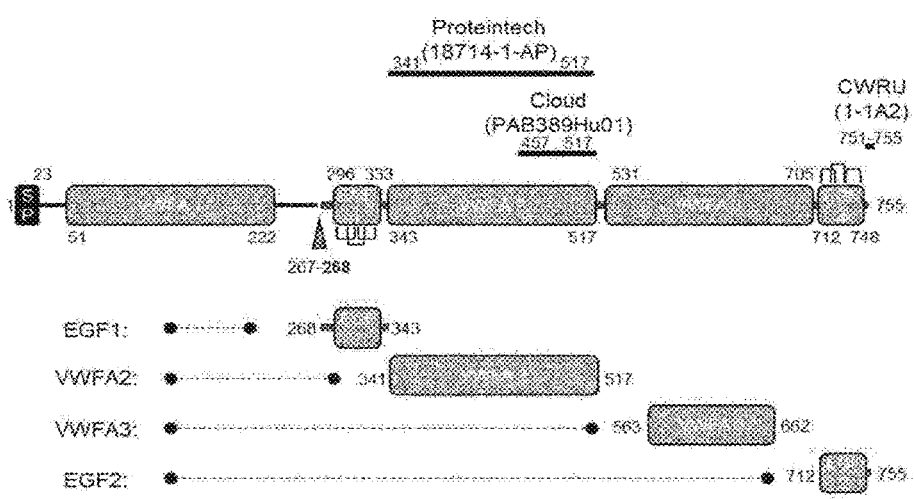
FIG. 13A is a schematic diagram illustrating the locations of CCSP2 antibodies per domain, and which domain is recognized by each CCSP-2 antibody.
FIG. 13B is western blotting results showing that the CWRU antibody specifically recognizes the EGF2 domain, and the Proteintech antibody specifically recognizes the VWFA2 domain.
Figure 13:
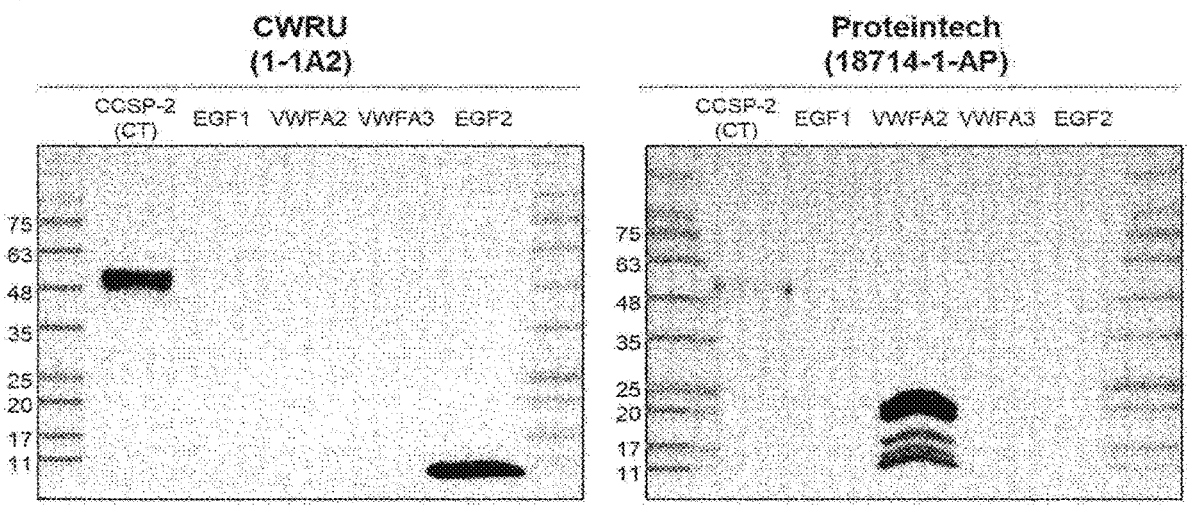

Referring to FIG. 13, it can be specifically confirmed that the CWRU antibody among the anti-CCSP-2 antibodies including the CWRU antibody, the Proteintech antibody and the Cloud-Clone antibody, specifically recognized the EGF2 domain (including up to amino acid 755 of CCSP-2), and the Proteintech antibody and the Cloud-Clone antibody specifically recognized the VWFA2 domain.

In addition, by applying an anti-CCSP2 antibody recognizing the EGF2 domain of CCSP2 and an anti-CCSP2 antibody not recognizing the EGF2 domain of CCSP2 to an immunostaining method, it was intended to confirm whether normal tissue can be clearly distinguished from a lesion.

To this end, first, CCSP-2 protein overexpression was induced in HeLa cells, and the CCSP-2-specific detection ability between the CWRU antibody and the Proteintech antibody was compared and analyzed by western blotting using the cell lysate thereof. While CCSP-2-specific detection of the CWRU antibody was possible according to the presence or absence of CCSP-2 expression, a non-specific signal was confirmed in the case of the Proteintech antibody regardless of CCSP-2 expression. In addition, paraffin blocks were manufactured by taking cancer tissue and normal colorectal tissue from a colorectal cancer patient, and analyzed by immunostaining using CCSP-2 expression-specific antibodies such as the CWRU antibody and the Proteintech antibody. The immunostaining method was carried out using an automated apparatus (Ventana Medical System), and the antibodies were reacted at a concentration of 1:100 for 32 minutes and then detected using the Nentana OptiView DAB kit. The CWRU antibody was not stained in normal tissue, but only stained in a lesion, whereas 50% of the Proteintech antibodies were stained even in normal tissue so that the Proteintech antibody did not clearly distinguish normal tissue from a lesion.

From this result, it can be presumed that the recognition of the amino acid sequence downstream the EGF2 domain specifically recognized by the CWRU antibody is effective for the purpose of distinguishing diseases, that is, normal tissue and a lesion. Based on this assumption, the inventors conducted antibody screening using a protein consisting of a sequence from the start of the EGF2 domain to the end of CCSP2 (the sequence of CCSP2 amino acids 712-755).

FIG. 14A shows western blotting results for comparatively analyzing the antigen (CCSP-2)-specific detection ability of the CWRU antibody and the Proteintech antibody in a cell lysate. FIG. 14B shows immunohistochemical results for comparatively analyzing the antigen (CCSP-2)-specific detection ability of the CWRU antibody and the Proteintech antibody in normal colorectal tissue and colorectal cancer tissue.

Figure 14:
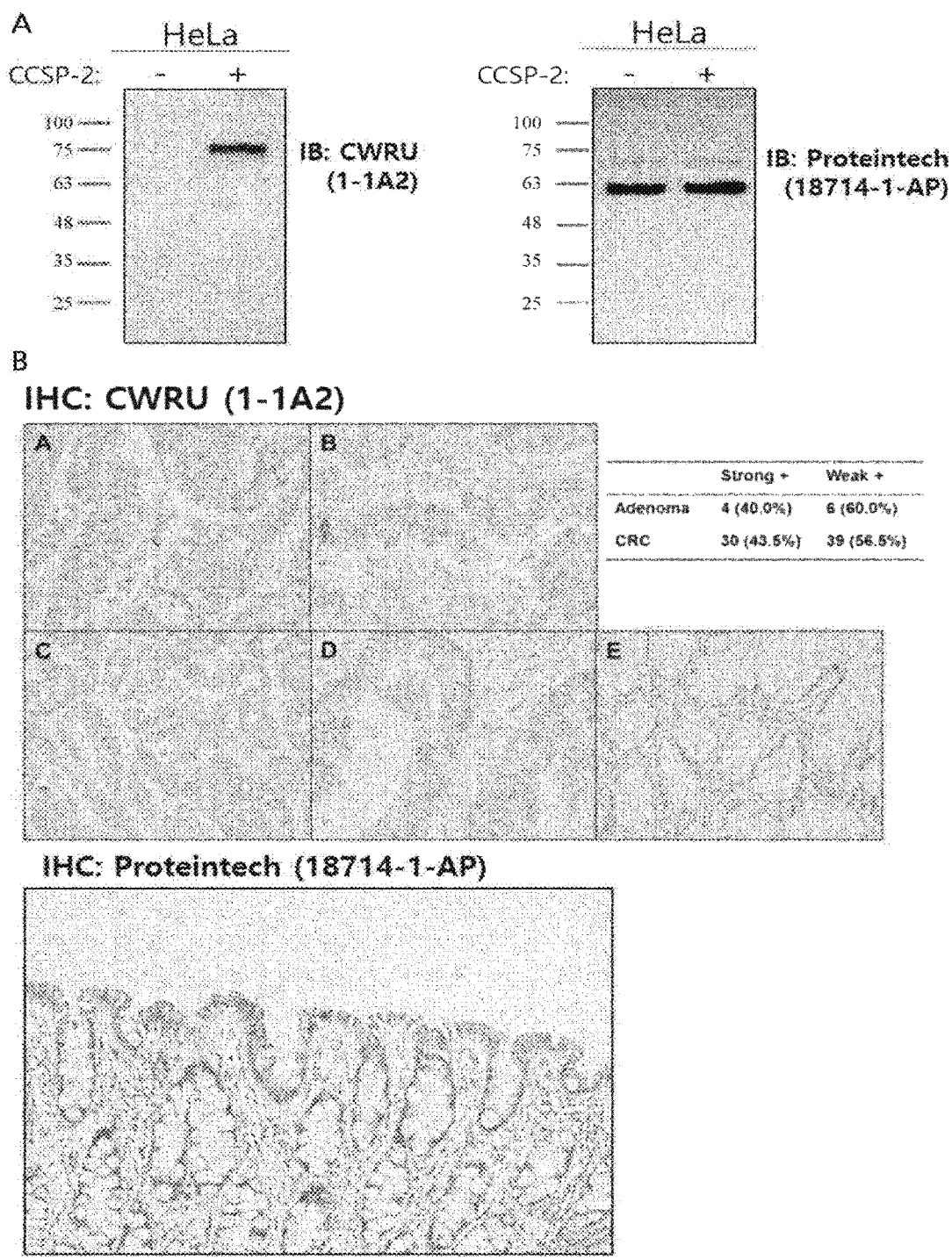
FIG. 14A shows western blotting results for comparatively analyzing the antigen (CCSP-2)-specific detection ability of the CWRU antibody and the Proteintech antibody in a cell lysate.
FIG. 14B shows immunohistochemical results for comparatively analyzing the antigen (CCSP-2)-specific detection ability of the CWRU antibody and the Proteintech antibody in normal colorectal tissue and colorectal cancer tissue.

Referring to FIG. 14, in the case treated with the antibody provided from Case Western Reserve University, it can be confirmed that none of the antibodies were stained in paired normal cells, and in the case treated with antibodies of the comparative example, it can be confirmed that approximately 50% of the antibodies were stained in paired normal cells.

That is, since the antibodies specifically binding to the EGF2 domain of CCSP-2 more clearly distinguish normal tissue from a lesion, compared with an anti-CCSP-2 antibody that cannot detect the conventional EGF2 domain, which is meaningful for distinguishing between the normal site and lesion, more accurate diagnosis is possible.

Figure 15:
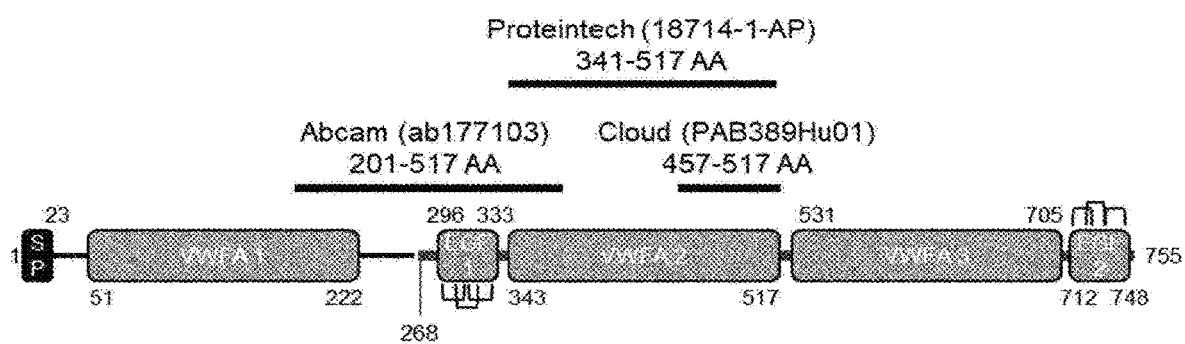
FIG. 15 is a schematic diagram for comparing the binding (detection) sites of anti-CCSP-2 antibodies which are currently available.

FIG. 15 is a schematic diagram for comparing the binding (detection) sites of anti-CCSP-2 antibodies which are currently available.

Referring to FIG. 15, since the Proteintech antibody binds to the sequence of amino acids 341-517 of CCSP-2, the Abcam antibody binds to the sequence of amino acids 201-373, and the Cloud-Clone antibody binds to the sequence of amino acids 457-517, the Proteintech, Abcam and Cloud-Clone antibodies are unable to detect the EGF2 domain, which is the sequence of amino acids 712-748 of CCSP-2, which is meaningful for distinguishing normal and lesion sites.

Experimental Example 2. Comparison of Affinity with Peptide Specifically Binding to Conventional CCSP-2

Affinity was compared between the antibody (scFv) according to the example of the present invention and a conventional peptide specifically binding to CCSP-2 (Korean Patent Application No. 10-2018-0060184).

However, due to the characteristics of materials for the peptide and the antibody, affinity was not able to be compared using the same experimental method. Therefore, for both the peptide and the antibody, the concentration range of the CCSP-2 protein was set, the binding ability between the peptide and the CCSP-2 protein was measured by FCS (Korean Patent Application No. 10-2018-0060184), and the binding ability between the antibody and the CCSP-2 protein was measured by ELISA (see Example 2-5-2 of the present invention), and then the dissociation constant was calculated.

Figure 16:
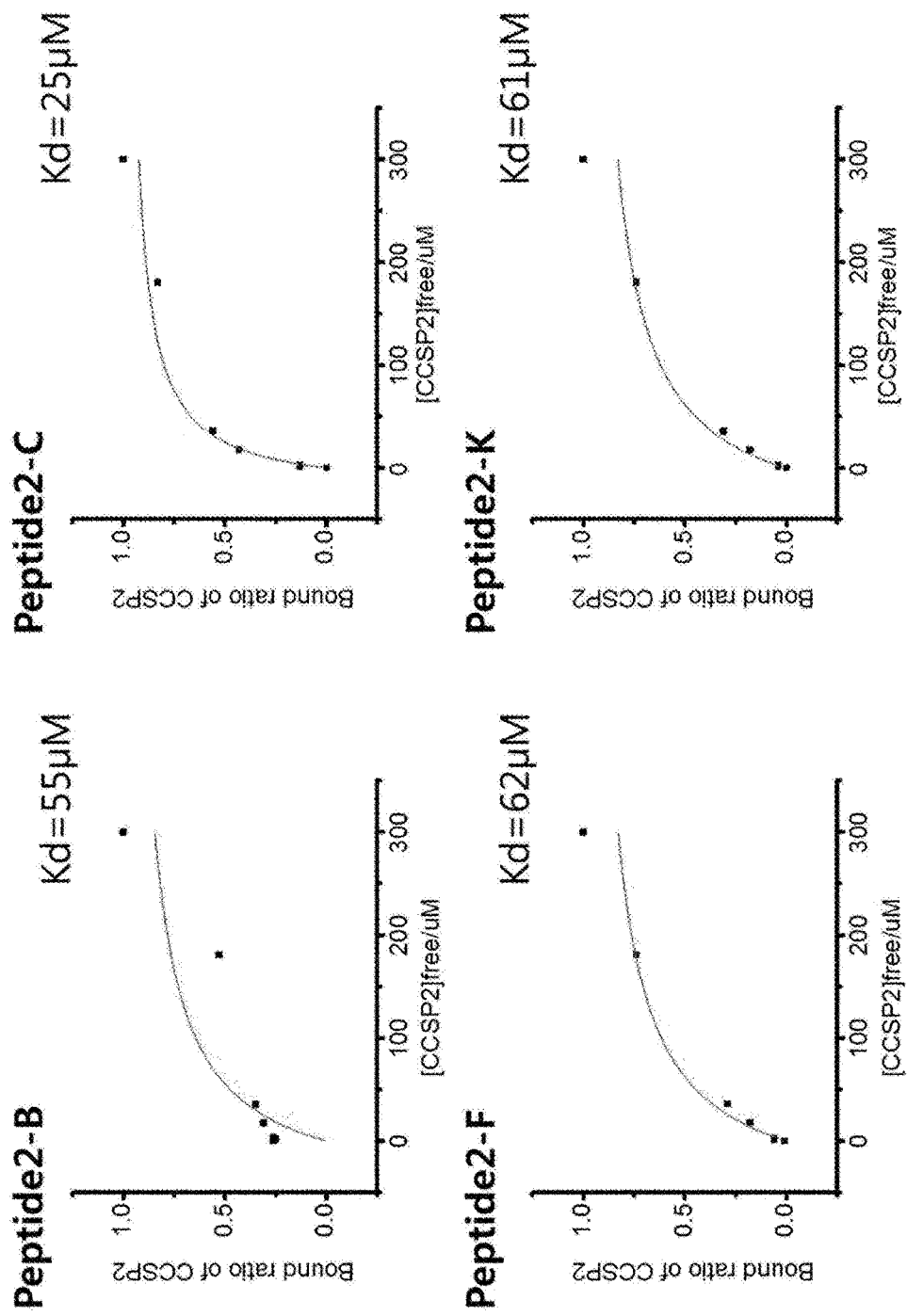
FIG. 16 is a set of graphs showing the affinity of the conventional peptides specifically binding to CCSP-2 (Korean Patent Application No. 10-2018-0060184).

FIG. 16 is a set of graphs showing the affinity of conventional peptides specifically binding to CCSP-2 (Korean Patent Application No. 10-2018-0060184).

Referring to FIG. 16, it can be confirmed that the KD value (affinity) for the binding of the conventional peptide and CCSP-2 is expressed in µM units.

Since the KD value (affinity) for the binding of the HN-1 (scFv) according to Example 1 of the present invention and CCSP-2 is expressed in nM units (see FIG. 1), it can be confirmed that the affinity of the antibody according to the present invention for CCSP-2 is considerably high.

Regarding the above description, it should be understood by those of ordinary skill in the art that the above description of the present application is exemplary, and the exemplary embodiments disclosed herein can be easily modified into other specific forms without changing the technical spirit or essential features of the present application. Therefore, it should be interpreted that the exemplary embodiments described above are exemplary in all aspects, and are not limitative. The scope of the present application is defined by the appended claims and encompasses all modifications and alterations derived from meanings, the scope and equivalents of the appended claims.

SEQUENCE LISTING FREE TEXT

SEQ ID NO: 1: VH CDR1 of HN-1
SEQ ID NO: 2: VH CDR2 of HN-1
SEQ ID NO: 3: VH CDR3 of HN-1
SEQ ID NO: 4: VL CDR1 of HN-1
SEQ ID NO: 5: VL CDR2 of HN-1
SEQ ID NO: 6: VL CDR3 of HN-1
SEQ ID NO: 7: VH CDR1 of CH-1
SEQ ID NO: 8: VH CDR2 of CH-1
SEQ ID NO: 9: VH CDR3 of CH-1
SEQ ID NO: 10: VL CDR1 of CH-1
SEQ ID NO: 11: VL CDR2 of CH-1
SEQ ID NO: 12: VL CDR3 of CH-1
SEQ ID NO: 13: VH CDR1 of CH-2
SEQ ID NO: 14: VH CDR2 of CH-2
SEQ ID NO: 15: VH CDR3 of CH-2
SEQ ID NO: 16: VL CDR1 of CH-2
SEQ ID NO: 17: VL CDR2 of CH-2
SEQ ID NO: 18: VL CDR3 of CH-2
SEQ ID NO: 19: VH CDR1 of CH-3
SEQ ID NO: 20: VH CDR2 of CH-3
SEQ ID NO: 21: VH CDR3 of CH-3
SEQ ID NO: 22: VL CDR1 of CH-3
SEQ ID NO: 23: VL CDR2 of CH-3
SEQ ID NO: 24: VL CDR3 of CH-3
SEQ ID NO: 25: VH of HN-1
SEQ ID NO: 26: VL of HN-1
SEQ ID NO: 27: VH of CH-1
SEQ ID NO: 28: VL of CH-1
SEQ ID NO: 29: VH of CH-2
SEQ ID NO: 30: VL of CH-2
SEQ ID NO: 31: VH of CH-3
SEQ ID NO: 32: VL of CH-3
SEQ ID NO: 33: HN-1
SEQ ID NO: 34: CH-1
SEQ ID NO: 35: CH-2
SEQ ID NO: 36: CH-3

The invention claimed is:

1. A monoclonal antibody specifically binding to the EGF2 domain of colon cancer secreted protein-2 (CCSP-2), which comprises heavy chain CDR1, 2, and 3 and light chain CDR1, 2, and 3,
wherein 1) the heavy chain CDR1, 2, and 3 comprises the amino acid sequence of SEQ ID NOs: 1, 2 and 3 respectively, and the light chain CDR1, 2, and 3 comprises the amino acid sequence of SEQ ID NOs: 4, 5, and 6 respectively, or
   2) the heavy chain CDR1, 2, and 3 comprises the amino acid sequence of SEQ ID NOs: 13, 14, and 15 respectively, and the light chain CDR1, 2, and 3 comprises the amino acid sequence of SEQ ID NOs: 16, 17, and 18 respectively.

2. The monoclonal antibody or the antigen-binding fragment thereof according to claim 1, wherein the antigen-binding fragment is selected from the group consisting of Fab, Fab', F(ab')2, scFv, Fv, dsFv, a diabody, Fd and Fd'.

3. A composition for diagnosing cancer, comprising the monoclonal antibody or the antigen-binding fragment thereof according to claim 1.

4. The composition of according to claim 3, wherein the cancer is selected from the group consisting of esophageal cancer, gastric cancer, colorectal cancer, rectal cancer, oral cancer, pharyngeal cancer, laryngeal cancer, lung cancer, colon cancer, breast cancer, cervical cancer, endometrial cancer, ovarian cancer, prostate cancer, testicular cancer, bladder cancer, kidney cancer, liver cancer, pancreatic cancer, bone cancer, connective tissue cancer, skin cancer, brain cancer, thyroid cancer, leukemia, Hodgkin's disease, soft tissue sarcoma, lymphoma and multiple myeloma hematologic cancer.

5. A composition for diagnosing cancer, comprising the monoclonal antibody or the antigen-binding fragment thereof according to claim 2.

6. A kit for cancer diagnosis, comprising the monoclonal antibody or the antigen-binding fragment thereof according to claim 1.

7. A method for diagnosing cancer, comprising:
   detecting colon cancer secreted protein-2 (CCSP-2) in a biological sample isolated from a subject suspected of having cancer using the monoclonal antibody or the antigen-binding fragment thereof according to claim 1 through an antigen-antibody reaction.

8. The method according to claim 7, wherein the cancer is selected from the group consisting of esophageal cancer, gastric cancer, colorectal cancer, rectal cancer, oral cancer, pharyngeal cancer, laryngeal cancer, lung cancer, colon cancer, breast cancer, cervical cancer, endometrial cancer, ovarian cancer, prostate cancer, testicular cancer, bladder cancer, kidney cancer, liver cancer, pancreatic cancer, bone cancer, connective tissue cancer, skin cancer, brain cancer, thyroid cancer, leukemia, Hodgkin's disease, soft tissue sarcoma, lymphoma, and multiple myeloma hematologic cancer.

* * * * *